United States Patent [19]

Seale

[11] Patent Number: 5,624,409
[45] Date of Patent: Apr. 29, 1997

[54] VARIABLE-PULSE DYNAMIC FLUID FLOW CONTROLLER

[75] Inventor: Joseph B. Seale, Gorham, Me.

[73] Assignee: FluidSense Corporation, Bedford, N.H.

[21] Appl. No.: 257,872

[22] Filed: Jun. 10, 1994

[51] Int. Cl.⁶ .................................................. A61M 5/00
[52] U.S. Cl. ............................................................ 604/246
[58] Field of Search ...................... 604/65–67, 246–247, 604/153, 30–34, 49–53, 118, 151; 128/DIG. 13, DIG. 12

[56] References Cited

U.S. PATENT DOCUMENTS

| | | | |
|---|---|---|---|
| 4,121,584 | 10/1978 | Turner et al. | 128/DIG. 13 |
| 4,204,538 | 5/1980 | Cannon | 604/246 |
| 4,207,871 | 6/1980 | Jenkins | 604/246 |
| 4,303,376 | 12/1981 | Siekmann . | |
| 4,826,482 | 5/1989 | Kamen | 604/246 |

*Primary Examiner*—Manuel Mendez
*Attorney, Agent, or Firm*—Chris A. Caseiro; Thomas L. Bohan

[57] ABSTRACT

A dynamic controller for quantitative rapid-pulse flow control over a wide dynamic range (1000-to-1) forms a fluid path from a pressurized source to a sink. The fluid path travels, typically in a disposable cassette, from the pressure source via a fast (one millisecond) on-off source control valve into a volume-displacement interface area, thence to a fast on-off load control valve and on to the sink. The load control valve may be replaced by a passive flow restrictor where less dynamic range is required. From the reusable controller side, fast actuators are energized to open the normally-closed valves. A volume sensor mates with the volume-displacement interface area. This sensor uses an incompressible transfer fluid, typically different than and isolated from the deliverable fluid by membranes, to transmit volume displacement change into a transducer area for conversion from volume to a measurable electrical signal, typically a frequency. A known pressure/volume curve for the volume sensor allows pressure monitoring during operation, yielding knowledge of fluid source and load conditions.

A flow control method relies on a combination of very short, variable valve-open pulses and design with comparatively large-diameter fluid passageways into the fluid capacitance of the volume sensor, to achieve flow limited more by inertia than viscosity. Distinct high-flow and low-flow control regimes are used. For high flow, bolus volume is maximized by pulsing for one-half the fluid oscillation period determined by the volume sensor fluid capacitance and the flow inertia of the fluid passageway, shutting off at flow reversal. For low flow, pulses typically below 10% of the high-flow pulse width yield small bolus volumes varying as the square of pulse width, providing control over a wide dynamic range of bolus sizes down to fractions of a microliter, permitting moderately high pulse frequencies even at very low average rates, achieving nearly continuous flow. Design with normally-closed, energize-to-open valves assures flow stop if power is lost. In this context, the large fluid passageways lead to a prescribed volume transfer at low valve-open duty cycle, conserving energy and making battery operation practical.

20 Claims, 7 Drawing Sheets

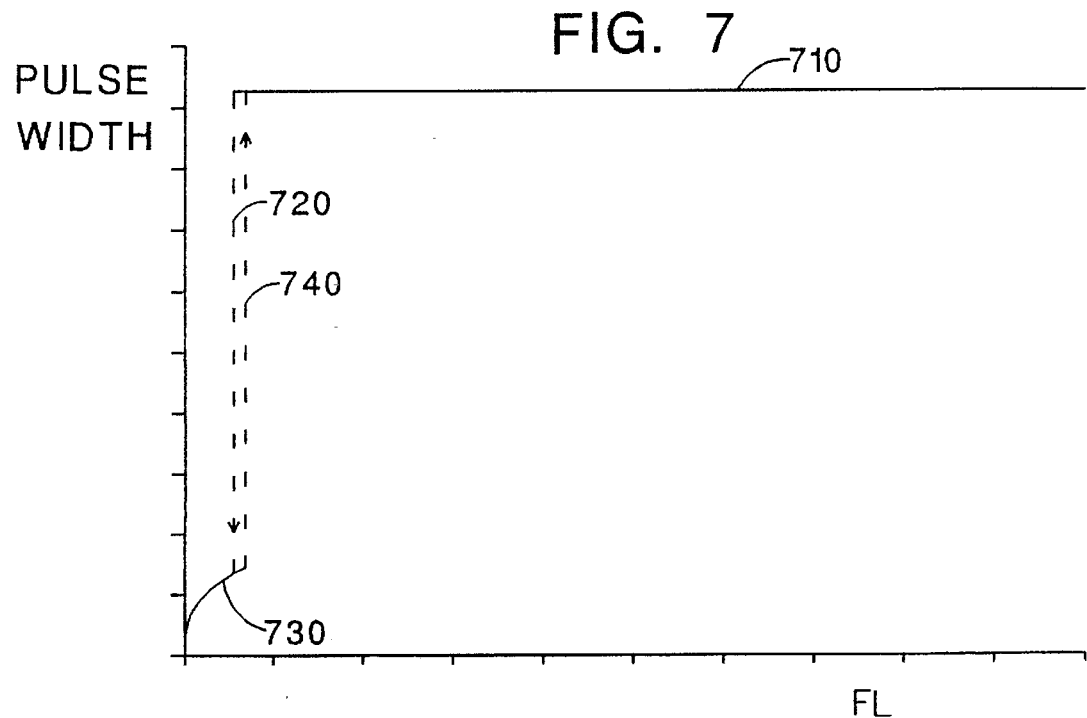
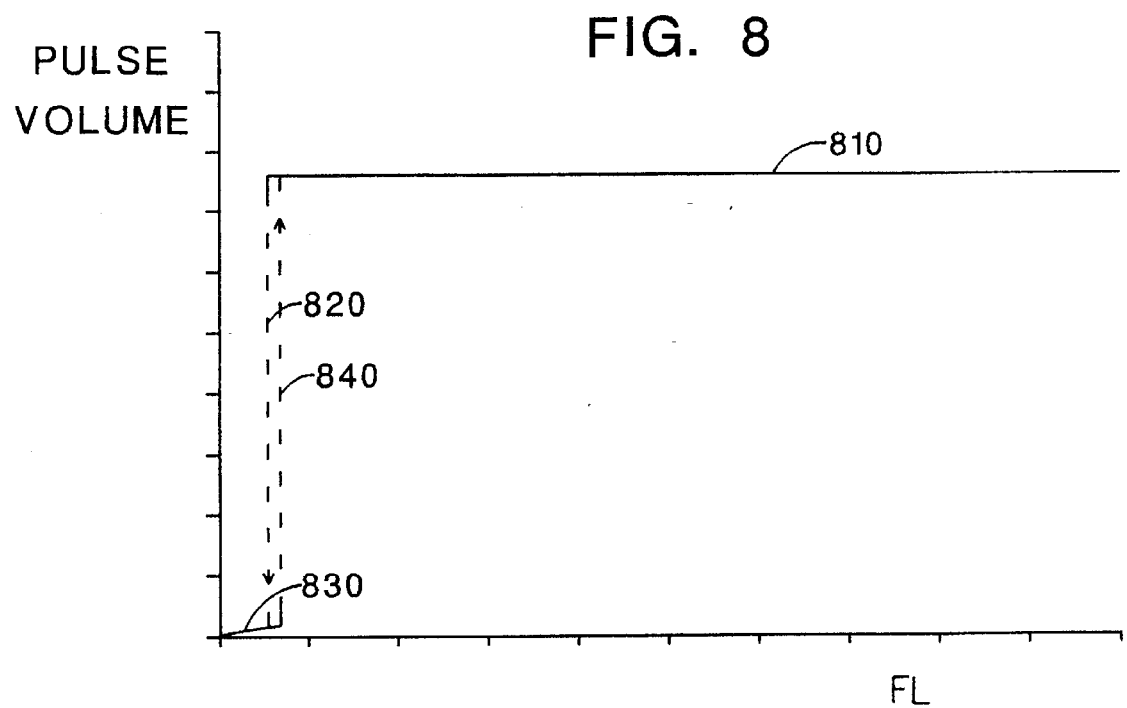

VARIABLE-PULSE DYNAMIC FLUID FLOW CONTROLLER

CROSS-REFERENCE TO RELATED PATENT APPLICATION

This invention is related to the Joseph B. Seale U.S. patent application Ser. No. 08/258,196 filed concurrently for CONVERSION OF LIQUID VOLUME, DENSITY, AND VISCOSITY TO FREQUENCY SIGNALS.

BACKGROUND OF THE INVENTION

1. Field of the Invention

The present invention relates to a device and a method for accurately controlling the flow of fluids through fluid delivery systems. More particularly, the present invention relates to a system and a method for controlling the rate of fluid flow over a wide dynamic range, relying in part upon extremely accurate measurement of the fluid removed from a source and delivered to a fluid sink.

2. Description of the Prior Art

In previous art, fixed fluid bolus volumes are transferred from a medical fluid source to a patient IV line via a cassette with inlet and outlet valves and an intermediate fluid chamber. In some systems the chamber volume is driven to vary abruptly over a fixed volume stroke, e.g., by positive and negative pressure pulses communicated across a flexible diaphragm (e.g., Siekmann, U.S. Pat. No. 4,303,376), delivering fixed boluses. If the stroke frequency is high enough, relative continuity of the output is achieved, but dynamic range of flow control is limited. At low rates, the interval between strokes becomes excessive and flow continuity is lost, and at high rates, a maximum practical operating frequency is reached. Better continuity of flow is achieved, e.g., in a system using an elastic "piston" consisting of plastic panels on "living" hinges, driven by a cam so that the intake stroke is fast and followed by a slow, steady discharge stroke. In this example, the price for flow continuity is greater mechanical complexity.

Looking toward greater simplicity, it is advantageous to use the energy present in the pressurization of a source fluid to deliver that fluid to a patient, e.g., as in the ReadyMED elastomer fluid reservoir. (ReadyMED is a registered trademark of IMED Corporation.) The disadvantage here is a stringent requirement for constant source pressure, implying high manufacturing cost, coupled with the inflexibility of a single delivery rate for a given device. Greater economy in the fluid source is achieved, e.g., with a minibag emptied by pressurized gas, but pressure in such a source varies widely during delivery. Similar comments apply to spring-loaded reservoirs. An active flow regulator could potentially compensate for source pressure variations, making more economical fluid pressure sources usable, while at the same time adding the flexibility of programmable flow rate. Seeking such a flow controller solution in the art, there are examples of active valve control (e.g. Peter, U.S. Pat. No. 5,049,141 or Idriss, U.S. Pat. No. 4,838,887) in systems where an elastic reservoir between active inlet and outlet control valves is alternately completely filled and completely emptied as the valves are alternately opened, thus achieving fluid boluses of known volume at a controllable bolus frequency. As with the push-pull pumping systems, fixed bolus size limits the dynamic range of infusion rate of the device, whereby low flow rates result in excessive time intervals between boluses and high flow rates result in high valve actuation frequencies and resulting excessive noise and power consumption.

OBJECTS OF THE PRESENT INVENTION

An object of the present invention not in prior art is to achieve programmatic infusion rate control from a variable or unregulated pressurized-fluid source over a very wide dynamic range, where, e.g., flow rates might vary from 0.5 to 400 milliliters per hour, and in such a manner that very small boluses of fluid are dispensed at the low end so as to maintain a predetermined minimum frequency of bolus deliveries as the average infusion rate is reduced and, alternately, to deliver much larger boluses of fluid at the high end so that valve actuation frequency is kept below a practical maximum (determined by power consumption, noise, and the maximum permissible speed of the valves.

A further object is to control and vary bolus size continuously through valve timing, substituting microprocessor timing control for the complicated mechanical valve-apparatus of the prior art.

A still further object is to operate a control valve for very short open pulses, such that fluid flow rate is effectively limited by fluid inertia rather than by viscosity, thereby achieving flow control insensitive to the large variations encountered in viscosity. (Densities of medical fluids vary considerably less than viscosities.) A related object, in a technique demanding short valve-open pulses, is to use comparatively large-diameter fluid passageways for high instantaneous flow rates, so that valve-open duty cycle can be kept very low and actuator duty cycle on normally-closed valves correspondingly low, as a means for minimizing electrical energy required during battery operation.

For delivery of large fluid boluses to achieve very high flow rates, an object of the invention is to match valve pulse widths to a natural fluid oscillation period of the system, permitting valve closure at a moment of near-zero flow rate and avoiding valve closure against a high flow, even as large boluses are delivered in short time intervals. Another object is to control flow with normally-closed valves that revert to a closed state when electrical power is lost, as a fail-safe measure. Using energize-to-open valves, the fluid-resonance-tuned operating mode permits near-equalization of cassette inlet and outlet pressures at a high flow rate while still requiring only a relatively low valve-open duty cycle, thus conserving battery energy.

A yet further object is to utilize a direct-volume conversion device which continuously measures incompressible fluid volume displacement, thus permitting accurate volumetric delivery in conjunction with the valving techniques indicated above. Such a direct volume conversion device is described in the referenced patent application "CONVERSION OF LIQUID VOLUME, DENSITY, AND VISCOSITY TO FREQUENCY SIGNALS" of Joseph B. Seale, Ser. No. 08/258,198, filed Jun. 10, 1994. That application will be referred to hereinafter as the Measurement System Application.

Related to the use of volume transduction, an object is to provide a cassette fluid interface design that matches displacements of a deliverable fluid with volume displacements in a separate volume transfer fluid in the volume transducer, independent of the particular range of shapes achieved by the stretching membranes that isolate the deliverable fluid from the volume transfer fluid.

These and other objects and advantages of the present invention will be apparent in the following specification and claims.

SUMMARY OF THE INVENTION

Fluid is propelled from a source to a sink by the source-to-sink pressure differential while the system of the present invention imposes precise volumetric regulation of flow pulses by active valve control and volume displacement measurement. A preferred means for this volume displacement measurement is described in the referenced Measurement System Application.

One embodiment of the present system utilizes valves upstream and downstream of the volume sensor, while a second embodiment utilizes a single upstream valve and a downstream flow path of high resistance, typically including one or two downstream flow restrictors functioning as fluid resistors with significant inertial components of impedance. In either embodiment, a normally-closed valve opens for a short enough interval that the valve-open flow rate is controlled in significant part by fluid inertia in an acceleration flow regime. Unlike capillary and pinhole orifice restrictors, which function as fluid resistors, the fluid pathways of the current invention are designed to function as fluid inductors, i.e. inertia-dominated flow impedances. The bolus volume through a fluid inductor varies as the square of valve-open time, yielding a wide ratio of bolus sizes (e.g., 100 to 1) for a smaller and more manageable ratio of valve pulse widths (e.g., 10 to 1). That is, when pressure is applied abruptly to a fluid inductor, that sets the first derivative to flow rate, which is the second derivative of volume with respect to time. Given a time duration, volume equals the second derivative of volume times one-half the square of the time interval. To achieve comparatively very large boluses while avoiding valve closure against a high flow momentum, the volumetric capacitance of the volume sensor is used to create a bounce in the flow rate, whereby flow rate crosses through zero at some interval after initial valve opening. By timing valve opening to match this interval, waterhammer problems at valve closure are avoided.

Combining a large-bolus zero-flow-shutoff regime with a small-variable-bolus, low-peak-flow regime results in a flow pulse algorithm that can span a very wide range of flow rates with a relatively small range of pulse rates. Fluid source and sink pressures are inferred from the swing in absolute volume measured at the volume sensor, utilizing a calibratable relationship between sensor volume and fluid pressure. Bolus sizes are inferred from volume sensor measurements.

In the noted two-valve embodiment, the bolus size inference is easy, for fluid volume in the volume displacement sensor can be held constant before and after bolus delivery for static measurements and subtraction of volumes to determine bolus size. In the second single-valve embodiment, flow via the restrictor to the load is uninterrupted as pulses of flow from the source replenish deliverable fluid volume in the displacement sensor. Where volume measurement requires a significant time interval (e.g., a millisecond or more, as opposed to a few microseconds), volume readings represent a time average of the changing signal. For interpreting time-smeared signals from a continuously varying volume displacement, a dynamic simulation model of the system is used to infer delivered volume and related interdependent quantities from observable volume displacement measurements, interpreted in conjunction with timing information about valve actuation. This simulation model can be an actual physical flow model, with multiple sensors and data acquisition, or it can be a computer simulation model. In practice, it is useful to have both the physical and computer models and to reconcile the two. The behavioral model, whether computer based or physical, is used to derive formulae, used in the design of embedded controller software, for backward inference from volume displacement measurements to delivered volumetric flow, as well as inference of other significant operating variances, especially source and load pressures.

BRIEF DESCRIPTION OF THE DRAWINGS

FIG. 7 illustrates valve pulse width as a function of the linear rate-controlling parameter of FIG. 6, again showing the mode transition with hysteresis.

FIG. 8 illustrates the bolus volumes corresponding to the pulse widths graphed in FIG. 7.

DESCRIPTION OF A PREFERRED EMBODIMENT

Figure 1A:
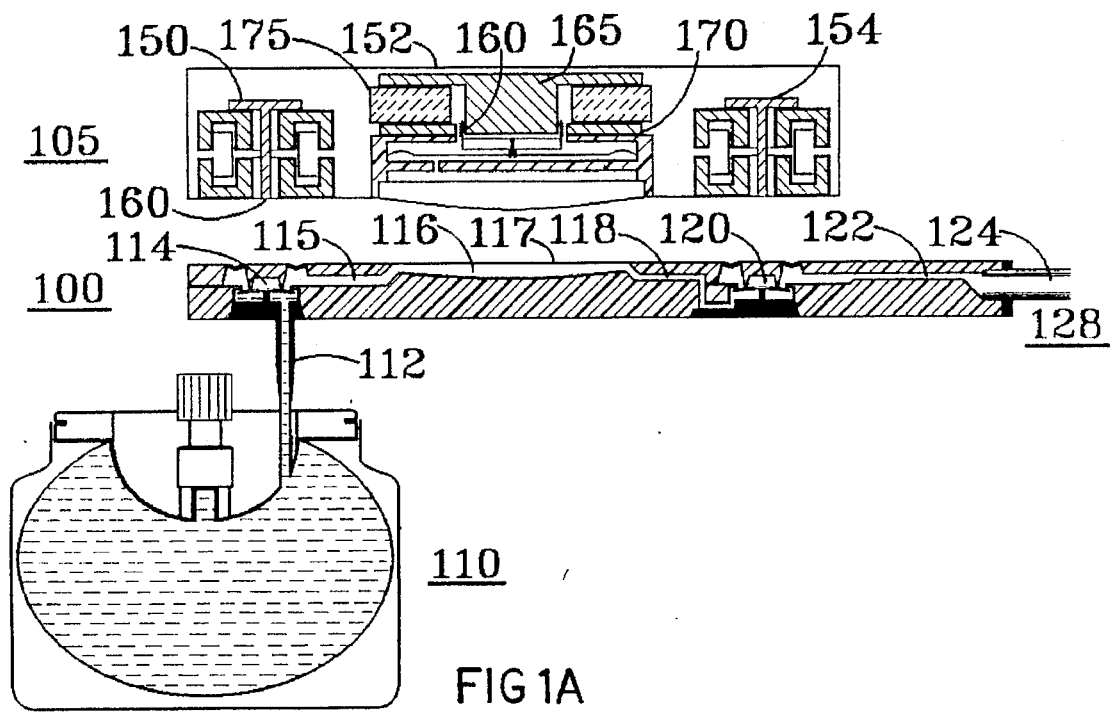
FIG. 1a illustrates semi-diagrammatically in section view the separated disposable cassette and reusable controller portions of a preferred embodiment of the invention.
Figure 1B:
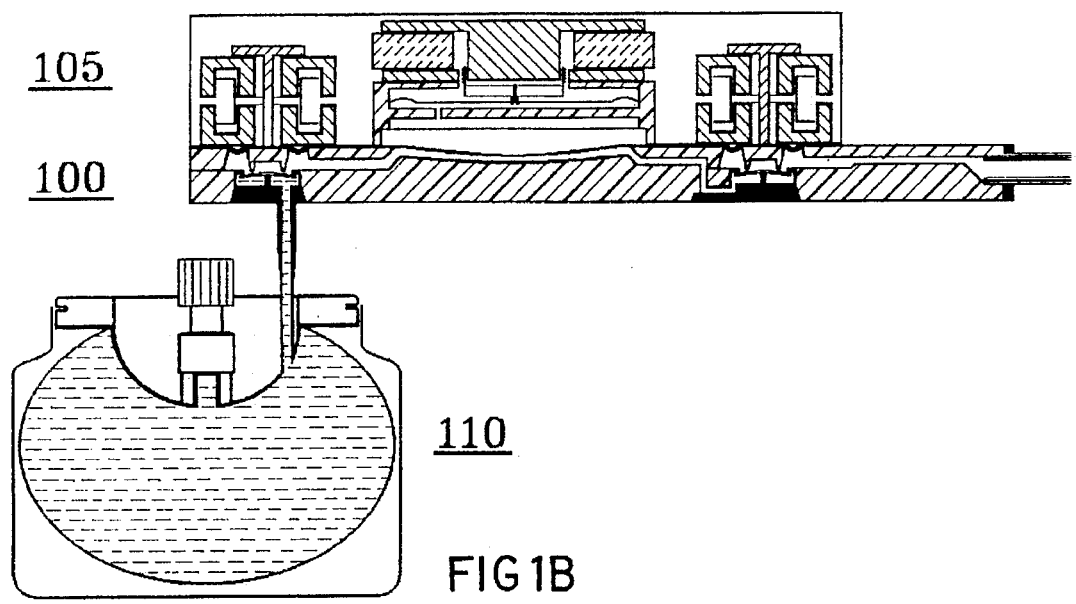
FIG. 1b illustrates the same components as FIG. 1a except with the controller and cassette joined in their operating juxtaposition.

The present invention is first summarized in a preferred embodiment with reference to FIGS. 1a and 1b, which illustrate the same components except for the separation (FIG. 1a) or joining (FIG. 1b) of cassette 100 and controller 105. Fluid flow is to be regulated programmatically between a source 110 of variable fluid pressure and a sink 128 (at the far end of the outlet tube, not shown) at lower variable fluid pressure. Regulation is to take place in the disposable fluid-carrying cassette 100 when operating in clamped contact with the reusable controller 105, as shown in FIG. 1b.

Cassette 100 receives from fluid source 110, here represented as a fluid-filled elastomer balloon, although any fluid source remaining within a suitable pressure range (e.g. 2 to 10 PSI) and not exhibiting excessive high-frequency variations in pressure (which could confuse the control algorithm) is likely to be suitable for the application described here. Deliverable fluid flows from this source at 110 through fluid channel 112, some fraction (including possibly a zero fraction) of which may be tubing and the remaining fraction of which may be part of cassette 100. Within this cassette, fluid enters the opening/closing component 114 of the source control valve and, when 114 is open, continues via channel 115 into compliant volume displacement interface 116. The fluid path exits this interface area via fluid channel 118, which extends into opening/closing component 120 of the load control valve. When 120 is open, the fluid path extends through channel 122 out of the cassette and into a region 124 of tubing which, for best system performance, should exhibit at least a minimum fluid volume/pressure compliance, as is discussed below. At the end of region 124 an optional flow restrictor, such as a length of microbore tubing or, alternatively, a pinhole restrictor may be included. The optional flow restrictor offers a safety feature in limiting flow rate, in the event that both valves fail in an open condition. It is to be noted that this flow restrictor is unnecessary to the functioning of the invention in this preferred embodiment, and the flow controller can adapt, in its servo control algorithm, to operation with or without this flow restrictor. Distal to tubing region 124 and the optional flow restrictor (if present) is an intravenous patient interface device, not shown, consisting of an inserted cannula or tube entering a vein. FIGS. 1a and 1b represent the patient interface device and the patient simply as fluid sink 128, beyond the end of tube 124, the sink having some associated fluid pressure. Though the preferred embodiment is configured as a patient infusion device, it will be seen that the system can provide fluid pulses to many fluid sinks, e.g., in automated fluid dispensers for industrial applications.

Illustrated in the upper portion of FIG. 1a, above cassette 100, is controller 105, which includes source solenoid thruster 150, direct volume conversion device 152, and load solenoid thruster 154. Also included along with these just-listed key elements, but not shown in the figure, are an electrical power source (e.g. batteries or a line-operated D.C. supply), a microprocessor, power switching electronics to drive thrusters 150 and 154 under control of the microprocessor, and interface electronics between the microprocessor and device 152. Two different embodiments of 152 are outlined below, similar in mechanical structure but differing in electronic and electromechanical construction and operation, yielding two corresponding descriptions for the interface electronics with 152. A more detailed description of the embodiments of 152 is found in the referenced Measurement System Application.

FIG. 1b illustrates the mating of disposable cassette 100 with controller 105. The description to follow is illustrated by both FIGS. 1a and 1b, the former for discerning separate components and the latter for seeing their functioning juxtaposition. Ignoring the details of flow dynamics, controller solenoid thruster 150 may be seen to be controllably activated to exert a force on cassette valve opening/closing component 114. 150 and 114 together constitute a two-state (full-open of full-closed) fast-response source control valve. The force exerted by 150 on 114 causes this normally-closed valve to open for a controlled duration. Fluid flows from source 110 via the open valve into interface area 116, where the increasing volume displaces a flexible interface, 117, causing a volume displacement in direct volume conversion device 152 accurately equal to the net volume flowing in through the valve. 152 converts volume to frequency according to a reproducible calibration function V(f), for volume V associated with measured frequency f. The starting and end point frequencies associated with the opening of valve component 114 therefore indicate the volume increment that flowed into the interface region. Similarly, opening of normally-closed valve component 120 under the influence of controller solenoid thruster 154 depletes the volume in the interface region, registering a volume decrease and measured fluid delivery to the patient when before-and-after frequencies f are plugged into the V(f) calibration function. The magnitudes of the resulting fluid pulses are controlled by pulse duration but do not, in general, vary in even approximately linear proportion to pulse duration for the geometry and pulse interval range of the preferred embodiment. The preferred embodiment employs larger-than-capillary fluid pathways (typically not much less than one millimeter diameter), with the result that volume transfer as a function of time after valve opening approximates a damped sinusoid (FIG. 5), starting out at zero rate-of-change at the moment of valve opening, going through an acceleration phase and, if permitted by a long, enough valve-open pulse, continuing into a deceleration phase up to a maximum achievable volume change. It is wasteful of valve actuation energy to extend a valve pulse beyond the natural period of one half-cycle of the flow response sinusoid, for any further increase in pulse duration only reduces the net volume transferred.

Figure 2A:
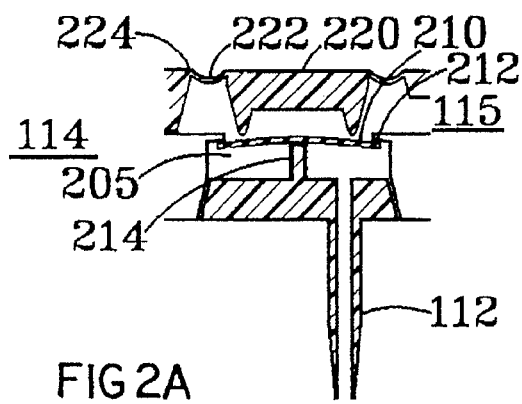
FIG. 2a illustrates in section view a normally-closed, solenoid-opened control valve in the disposable cassette, in its closed position.
Figure 2B:
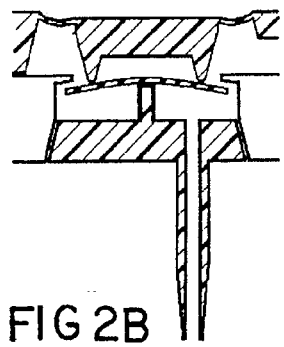
FIG. 2b illustrates the valve of FIG. 2a in its open position.

Examining the physical geometries that determine the nature of the damped sinusoid response just mentioned, which readily becomes more-than-critically damped and exponential in nature if the fluid passageways are too narrow, we consider the net fluid inertia of path 112, of open valve component 114, and of fluid path 115 to "capacitor" 116. Or similarly, we consider the net fluid inertia from 116 in fluid path 118, through open valve component 120, and continuing in fluid path 122, into a load. This fluid inertia, along with flow resistance, couples with the fluid capacitance of 116. Thus, the fluid path when 114 opens and/or when 120 opens behaves as a fluid LCR (L=inductor, C=capacitor, R=resistor) circuit. The response to opening of 120 may be further complicated by the pulse wave guide nature of tube 124 and other characteristics of the load, including possible flow restrictor 126. The dynamics just described will be discussed in more detail with reference to the impedance schematic of FIG. 4. First, we consider more closely the valve and displacement sensor components of FIGS. 1a and 1b. Referring to FIGS. 2a and 2b, we observe the opening/closing valve component 114 of cassette 100. Component 120 is similarly constructed. In FIG. 2a, 114 is closed, while in FIG. 2b, 114 is open. The figures are otherwise the same. The design begins with a valve structure that resembles a passive one-way check valve, oriented here to be closed against flow rising from below via passageway 112 into cavity 205 and to open, at some forward cracking pressure, when pressure in passageway 115 exceeds the pressure in 205. As an active servo-valve, 114 operates for flow in the normally-checked reverse direction. Elastomer disk 210 seats on lip 212 in response to a reverse bias, isolating cavity 205 below from passageway 115 above. At zero and small forward biases below the cracking pressure, the preload bending of 210 by the upward thrust of center post 214 maintains 210 seated. At sufficient forward bias, with pressure in 115 above exceeding pressure in 205 below, the edges of disk 210 deflect downward as in the disk of FIG. 2b, opening a crack over at least part of the perimeter of 210 with respect to lip 212 and permitting fluid flow. In the present invention, this forward cracking pressure is seldom or never achieved in normal operation and reverse pressure is the norm. As is described below, forward cracking my occur immediately following maximum-bolus flow pulses in a system with a high source to load pressure differential and a significant pressure overshoot in its dynamics.

In the active valve configuration shown, cup 220 is held by circumferential "living" hinge 222 in relation to the. surrounding region 224 of the cassette. 222 is a thin plastic annulus, curving axially downward (as illustrated, though upward curvature would work) and back upward along any radial path from the inside to the outside diameter of the thin annulus. When cup 220 is pushed down from above by thruster rod 160 of solenoid driver 150 (see FIGS. 1a and 1b), annulus 222 bends near the inner and outer perimeters and flattens somewhat in the middle to permit 220 to move down, as shown in FIG. 2b. The rim of 220 then contacts disk 210 slightly inside of lip 212, and pushes down the edge of the disk, unseating it as illustrated. The thruster must overcome elastic forces in the living hinge, pressure forces associated with the area of 210 and the differential between pressure in 205 and pressure in 115, and pressure forces associated with the area of 220 plus part of the area of annular hinge 222 and the pressure differential between 115 and the environment above 220. A further increment of force is needed to overcome the pretension associated with the curvature of disk 210 and bend that disk to greater curvature. The valve geometry is small and the travel of 220 to open the valve is short, typically less than 0.020 inches to carry 220 from rest position out of contact with 212 into a full-down position with 212 unseated sufficiently for the valve opening to offer negligible flow resistance, compared to the largely inertial impedance of fluid-filled passageways leading to and from the valve. Solenoid thruster 150 is designed to accomplish this travel in roughly one millisecond, with the return transit time being similar, depending on the altered pressures in 205 and 115 after 210 is unseated and the valve effectively opened. The structure of valve opening/closing component 120 is the same as 114 except for differences in the connection of fluid passageway 118, as contrasted with 112, into the cavity below the disk.

Thruster solenoids 150 and 154 are diagrammed based on the geometry and scale of potentiometer cores (pot cores) that can be modified to function as solenoids in the current invention. Wound bobbins are indicated in the centers of the pot cores, with axial magnetic gaps that are drawn toward closure when an electric current passes through the bobbin winding. With the bottom half of either pot core fixed and the top half able to travel downward, the excited magnetic field pulls the top half down, driving down thruster rod 160 of solenoid 150 or its counterpart in solenoid 154. In typical operation, a very substantial current pulse will be used to initiate the solenoid thrust to close the valve, driving the pot cores to near-saturation at a high instantaneous coil wattage—typically a few watts. Within a millisecond or so, when the magnetic gap is close, a much lower current is required to maintain the same field strength and the same closing force, since the torroidal magnetic circuit is now entirely through high-permeability core material with no significant remaining air gap. A practical reduction of 5-to-1 in current to maintain force on the closed solenoid gap represents a reduction of 5-squared or 25-to-1 in coil power, though with the most obvious series voltage regulator design from a fixed-voltage supply, only a 5-to-1 power saving is realized. With more sophisticated electronics based on dual supply voltages or pulse width modulation to drive the solenoid, power savings coming closer to 25-to-1 can be accomplished—details beyond the scope of this description and concerning efficiency optimization that is not essential to the fundamental operation of the current invention.

The action of solenoids 150 and 154 can be accomplished by other transducer approaches. A very simple approach, though not offering the combined compactness and efficiency of a good solenoid design, is to use a voice coil driver to provide the desired thrust Such an approach minimizes moving mass for quick response, but efficient operation demands a substantial permanent magnet. Another approach is to derive thrust from a piezoelectric bender or bender stack. The thrust involved is within reach of bender stack technology, though somewhat expensive to achieve and demanding of a high supply voltage to drive the bender. Electromechanical efficiency of the piezoelectric approach for this application is fairly good.

Figure 3:
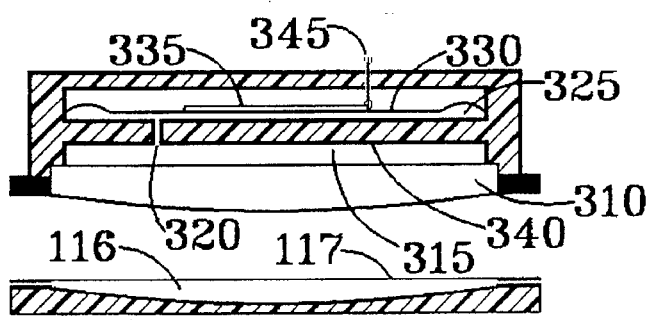
FIG. 3 illustrates in section view a direct volume conversion sensor above the cassette mating membrane, the sensor producing a volume-sensing vibration frequency utilizing a piezoelectric disk transducer.

The volume displacement sensor in a preferred embodiment is illustrated in FIG. 3, which is discussed briefly here. FIG. 3 shows a volume transfer fluid 315 isolated from the deliverable fluid in the volume displacement area 116 of the cassette by two barriers: 117, an elastic barrier that is part of the cassette and contains the deliverable fluid; and 310, an elastic barrier that is part of the controller and contains the volume transfer fluid. Barrier 310 is shown not as a membrane, but rather a comparatively thick elastomer plug, being proportioned to hold its shape and present a convex surface upon mating with membrane 117. The footprint where the convex surface of 310 meets 117 spreads from a point of initial contact to cover the entire interface area, with the objective of leaving no air pockets. The preload shape of 310 pushes 117 into cavity 116 at low fluid pressure, displacing some fluid out of the cassette. When the cassette is pressurized from the source, the high end of the pressurization range will deflect the; lower surface of 310 to flatness and on to concavity. For maximum utilization of membrane 117 to achieve volume displacement, a symmetric swing from convex-down to convex-up achieves the greatest volume transfer for a given membrane stretch. In some contexts, barriers 117 and 310 may be omitted, in which case fluid volume transfer fluid 315 will be part of the deliverable fluid. Properties of the deliverable fluid will affect the volume displacement measurement process, but in some contexts, fluid property variations will be of minimal significance.

Whether or not the volume transfer fluid is distinct from the deliverable fluid and isolated by fluid barriers, the volume displacement sensor, called "DVC" for "Direct Volume Converter," must be purged of air or any other uncontrolled quantity of compressible gas to function properly. The potential problem is that gas inclusion in either the deliverable fluid or the volume transfer fluid adds an extra compliance, altering the relationship of volume displaced into the sensor area to either pressure change or deflection of sensing elements. Gas may be present and interacting with fluid volume change only if it is present in a controlled volume, e.g., for the intended purpose of adding a known volumetric compliance.

The volume transfer fluid (which may or may not be distinct from the deliverable fluid) communicates from region 315 via orifice 320 with region 325, where fluid is captured between rigid surface 340 and spring plate 330. As is explained in more detail in the referenced Measurement System Application, plate 330 performs dual functions: as a volume displacement spring, giving a repeatable curve relating pressure to volume displacement; and as a resonator plate whose resonance frequencies are sensitive to the plate distortions associated with fluid volume displacement. More specifically, as fluid enters cavity 325 beneath the plate via 320, the plate surface is deformed upward while the fluid layer between 330 and 340 thickens. In a number of resonant modes, including the lowest-frequency mode (which is convenient to use for volume sensing), vibratory bending in the plate stores elastic potential energy Ep in the plate, while the motion of unbending (and passing through a shape of minimum elastic energy) entrains radial fluid motion under the plate, e.g., with fluid in the thin layer moving radially outward as the center of plate 330 descends while the perimeter region rises. The kinetic energy Ek of fluid motion beneath the plate, in relation to the rising and falling velocity V of the center of the plate in a specified vibration mode can be related by effective mass, M, by:

$$Ek=\tfrac{1}{2}*M*V^2 \qquad [1]$$

where "$V^2$" designates "V squared", the square of velocity, and "*" designates multiplication. The potential energy Ep stored in the plate can be related to the displacement X of the center of the plate away from equilibrium by an effective spring constant K according to the formula:

$$Ep=\tfrac{1}{2}*K*X^2 \qquad [2]$$

If we further specify that velocity V is defined for the same point whose displacement from equilibrium is measured by X, i.e. if we have the derivative relation:

$$V=dX/dt \qquad [3]$$

between V and X with variation in time t, then We will have for small linear perturbations of the plate the angular frequency formula:

$$\text{OMEGA}=\text{SQRT}\ (K/M) \qquad [4]$$

for angular frequency OMEGA as the square root of K divided by M. The effective mass M varies roughly as:

$$M=M0+RHO*M1/Q \qquad [5]$$

where M0 is an effective mass associated with the plate, RHO is the density of the volume transfer fluid under the plate, M1 is a coefficient relating to the plate geometry, and Q is the volume of fluid captured in the thin layer between the plate and the rigid surface below the plate. In a practical design, the constant term M0 is substantially smaller than the volume-sensitive RHO*M1/Q term. It is seen that Eqs. 4 and 5 together imply a formula for relating frequency to volume. A complication is that the small-perturbation spring constant K is not constant, but varies with volume roughly as:

$$K=K0+K1*Q^2 \qquad [6]$$

where the volume-squared coefficient K1 exists because the plate is least stiff when it is flat and becomes stiffer as fluid accumulating under the plate bends the surface into a curve. It is seen, therefore, that frequency OMEGA rises with increasing volume Q because of two combined effects, the thickening of the fluid layer lowering effective fluid inertia, and the nonlinear stiffening of the plate as pressure bends its surface toward greater curvature. A pre-curved plate will behave differently than an initially flat plate. The ultimate volume versus frequency calibration curve is best derived empirically, after mathematical formulas like the above have guided the designer to a useful range of frequency and pressure/volume compliance. Observe that plate 330, as drawn, includes a flat center region and an annular bump near the outer perimeter. The annular bump permits greater deflection of the plate surface by volume change without developing excessive stress or pressure change. For small static perturbations, a completely flat plate is more compliant than the ridged plate drawn, but for large perturbations, tension in the bowing flat plate quickly dominates over bending stresses in the surface, giving rise to a cube-law term relating pressure to volume increase. In a formed, ridged plate as drawn, the linear pressure/volume coefficient is higher, while the cube-law coefficient is substantially smaller, permitting much larger volume perturbations in a comparatively linear region.

The resonant frequency of the plate can be determined electronically by coupling to the plate an electromechanical transducer capable of exciting a volume-sensitive resonant mode. The mechanical resonance feature will be mirrored by a feature in the electrical impedance versus frequency function of the transducer. In FIG. 3, the electromechanical transducer is indicated as a thin piezoelectric ceramic disk 335 laminated to the center region of plate 330, with twisted wires 345 communicating between conductive surfaces on 335 and oscillator circuitry not shown. The disk-plate lamination shown will be recognized as a piezoelectric bender configured like a buzzer, such as is found in many smoke alarms, telephones, pager beepers, etc. In such devices, it is common to have three leads connected to the piezoelectric plate, a common ground, a power lead to most of the surface opposite the ground for driving the vibration, and a sense lead to a smaller electrically isolated area opposite the common ground for detecting the voltage or charge displacement caused by bending in the plate. A regenerative feedback circuit from the sense lead to the power lead sets up oscillations at the mechanical resonance frequency. In the present context, the oscillation amplitude should be kept quite small to avoid excessive noise generation and to avoid amplitude-dependent nonlinear perturbations in frequency. There will be elastic non-linearity in relation to volume change, which is incorporated into the volume-versus-frequency calibration function, and calibration would be further complicated if vibration amplitudes were large enough to cause further frequency perturbations.

Piezoelectric excitation is not the only applicable transducer approach. FIG. 1a illustrates a voice coil driver coupled via a small screw and nut to the center of the vibrating plate. The left side of the; cross-section of the circular voice coil is indicated at 160 (FIG. 1a), the coil moving in a magnetic field gap between center iron piece 165 (which is a plate on top extending down into a post going into the middle of the coil) and annular iron plate 170, the field being generated by ceramic magnet 175 sandwiched between 165 and 170 in a conventional voice coil driver configuration. The easiest way to obtain regenerative oscillation with a voice coil driver is to include a velocity-sense winding along with the primary driver winding (as is done in some integrated loudspeaker/amplifier designs). Voltage in the sense winding will be proportional to coil velocity. Alternatively, a voltage proportional to voice coil velocity can be detected directly in a single-winding voice coil, e.g., by placing the voice coil in a balanced bridge circuit designed to null the differential output signal from the bridge when the voice coil is not moving. This bridge circuit then yields a velocity indication as its imbalance output. By feeding the velocity signal, however obtained, back via power amplification so that a current flows in the main winding in phase with the sensed velocity-dependent voltage (either from the sense winding or from the bridge circuit), a negative electromechanical damping can be obtained, giving rise to a regenerative oscillation: In either piezoelectric or voice coil oscillator circuits, automatic gain control can be used to regulate amplitudes and avoid overloads, or phase-lock-loop circuitry can be employed to provide a drive signal in phase with the transducer velocity response, generating in either case an output frequency that tracks the mechanical resonance.

The plate could be excited by a moving magnet rather than a moving coil transducer, or indeed by any transducer capable of transforming back and forth between electrical and mechanical energy and interacting with the resonance of the plate. Note that the Direct Volume Converter design, as a whole, is not a true transducer between volume change and electrical energy, because pressure-times-volume energy does not translate directly or reversibly into charge-times-voltage energy on the electrical side in the normal volume-sensing mode of operation. Rather, low-frequency volume changes alter the conditions under which a high-frequency transducer-mediated oscillation takes place, with the resulting frequency being useful for volume sensing. To illustrate the irreversibility in going from volume to frequency, a mechanical volume change will not generate a resonance-frequency output from the transducer, in the absence of regenerative or phase-lock electronics. Neither will a driven vibration-mode resonance couple to generate a DC volume or pressure change, except possibly as a nonlinear effect at very high vibration amplitude. A true transducer includes some component of passive, reversible transformation of energy between two forms, e.g., electrical to mechanical and back to electrical. (A resistive strain gauge sensor is another example of a sensor that is a signal converter but not a transducer.)

Note in FIG. 3 that hole 320 communicating between fluid in 315 and fluid in 325 is off-center. The hole is intentionally placed as near as possible to a pressure node for the plate vibration mode being used in volume sensing. This minimizes the coupling between the plate, in its oscillatory vibration mode, and any mechanical load properties associated with cavity 315 and things coupled to 315, so that oscillation frequency is unaffected by conditions outside cavity 325. This hole location minimizes the effect of any environmental noise that might interfere with the sensed oscillation. This location of hole 320 also helps minimize unwanted noise coupling away from the plate into the outside environment.

The Direct Volume Converter design just described here briefly is not the only applicable form of volume sensor for a fluid flow controller. The DVC design is primarily a volume sensor, by the physical nature of the alterable inertia of a captured volume of water in a fluid layer between plate 330 and surface 340, and secondarily it is a pressure sensor, by virtue of the consistent spring response of the plate to give a change in pressure for a change in volume. Pressure is calibratable, while volume response is likely to be more consistent and stable than pressure response. One can, however, design a volume spring, i.e. an apparatus that gives a consistent pressure versus volume relationship, and attach a conventional pressure transducer to the volume spring to obtain a volume displacement sensor usable in the current invention. An example of such a device would be spring plate 320 over rigid plate 340 functioning as a non-vibrating volumetric compliance for the total fluid quantity in region 325. Coupling region 325 to a DC-responding pressure transducer would then constitute a volume displacement sensor. While the DVC design was optimized for the context of the current invention, it is not the only sensor adequate to the task.

Figure 4:
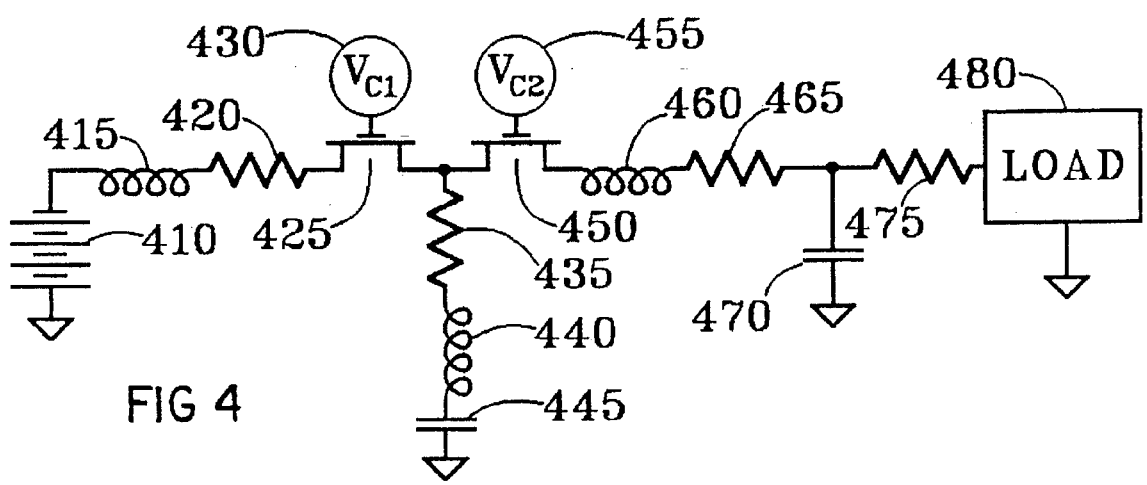
FIG. 4 shows an electronic circuit schematic analogue of fluid flow dynamics in the controller of FIG. 1.

Moving to FIG. 4, an electronic circuit schematic whose current/voltage relationships are analogues of the flow/pressure relationships in cassette 100 of FIGS. 1a and 1b. Looking at FIGS. 1a, 1b, and 4 together, battery 410, grounded at its negative terminal, delivers a positive voltage that is analogous to pressure P from fluid source 110. Fluid channel 112 may be characterized by an effective flow inertia and fluid-ohmic resistance, represented respectively by inductor 415 and resistor 420. Valve opening/closing component 114 is analogous to the channel in field-effect transistor 425, while thruster shaft 160 of solenoid 150 functions as control voltage Vc1, at 430, coupled through the gate of the transistor to turn the transistor full-on or full-off. The volume displacement sensor including cavity 116 and the apparatus coupled above 116 is represented by series resistor 435, inductor 440, and capacitor 445, which is grounded on the other side. Capacitor 445 represents the volume/pressure compliance of the volume displacement sensor. The volume-sensing function of the sensor amounts to detecting the charge on capacitor 445 (e.g. by measuring the voltage across the capacitor and multiplying by the capacitance) and converting the measurement into an appropriate output signal (e.g., voltage-to-frequency conversion for analogy to a volume-to-frequency converter). There is some flow impedance into and out of the volume sensor, e.g., via hole 320, which is represented by the inductor-series-resistor combination of 440 and 435, all in series with capacitor 445. Valve opening/closing component 120 is analogous to the channel in field effect transistor 450, with the actuation via control voltage Vc2 at 455 via the gate of the transistor analogous to the actuation of solenoid assembly 154. Flow inertia in channel segments 118 and 122 is collectively represented by inductor 460. Flow resistance in segments 118 and 122 sum to give part of the resistance in resistor 465. Tube 124 is represented by the remaining resistance in 465 and the capacitance in 470, which is returned to ground on the opposite side.

The impedance of tube 124 is actually more complicated than the schematic suggests, as is discussed below, although the circuit schematic representation presented is adequate to analyze the essential functioning of 124 in the current system context. At the fluid delivery end is likely to be some significant flow resistance, e.g., a cannula. In the preferred embodiment, a flow restrictor, e.g., microbore tubing, is placed at the load end of tube 124. The net resistance at the load end, including the flow restrictor if any, is represented by resistor 475. The load itself, represented by box 480 connected between the "distal" side of resistor 475 and ground, may present "ground" potential to the termination of 475, i.e. zero gauge pressure, or it might present a time-varying potential, representing, e.g., the pulsating artery of a patient or a vein in an arm that is going up and down, causing a variation in head height.

To model the impedance to tube 124 properly, one must take account of its wave propagation properties. For quick discharge from capacitance 445 via valve channel 450 into the tube, it is necessary that tube 124 be physically relatively large and of some significant compliance. A standard PVC tube with 0.065 inch inside diameter and 0.125 inch outside diameter is of an appropriate scale, while the substantially smaller tubing used in some IV sets will not be compatible with short valve pulses. Regardless of the volumetric compliance that the tube set offers, as represented by capacitor 470, this compliance is not "seen" by the controller output over a flow pulse duration of 50 milliseconds or less, 50 milliseconds representing about the longest pulse time scale anticipated for most applications of the current invention.

The 0.125 inch outside diameter PVC tube just mentioned, for example, if flexible enough to expand in inside, diameter by 15% under a pressure increase of 10 psi (this expansion being highly dependent on the PVC formulation, age, etc.), will exhibit a wave propagation velocity on the order of 15 meters/second, along with a fairly rapid dispersion and blunting of the wavefront due to damping components of the tube elasticity. This implies that over 50 milliseconds, only 30 centimeters of tubing length will have expanded in response to the flow pulse from the proximal side, while any remaining length will not have felt the pulse arrival. The impedance at the tube inlet will not "feel" the effect of the far end of the tube until the pulse wave has propagated all the way to the far end and reflected back, implying that over a 50 millisecond pulse, flow into the tube set will not be affected by a tube termination any farther than 15 centimeters from the proximal end. For input pulses into an essentially "infinite" tube length, i.e. long enough for there to be no reflections from the distal termination over a valve pulse period, the flow impedance at the proximal end of the tube is substantially resistive. This is not because of dissipative tubing resistance, but because flow energy into the tube creates a propagating wave that carries elastic and kinetic energy with it. This kind of wave propagation has been well studied in arteries. The situation is analogous to feeding an electrical pulse into a long coaxial cable. If the characteristic wave impedance of the coax is 75 ohms, then the resistance to a short pulse into the cable will be 75 ohms until such time as a reflection returns from the far end. In the case of our 0.065 inch inside diameter tube with 15% increase in inside diameter over a 10 psi pressure increase, the mathematics (presented below) imply a wave impedance of about $7*10^9$ Pa/(M$^3$/S), which is substantial but not totally dominating in relation to practical resistance values likely to arise in the resistors of FIG. 4.

Concluding this discussion of tube impedance, assuming that a wave pulse does not travel far enough to hit resistor 475 and bounce back to resistor 465 during the valve-open interval, then the proper representation for flow during the pulse is to terminate resistor 465 into a constant potential (i.e. pressure) for the duration of the pulse, i.e. as if the impedance of capacitor 470 were zero, but recalling that the tubing wave impedance has been included in the value of resistor 465. After the pulse is over and the waves in the tube have settled down, the proper value for capacitor 470 will be the volumetric compliance of the entire length of tube 124, and the increment of charge (i.e. volume) into that capacitance during the flow pulse will be simply the charge that flowed out of capacitor 445 during the pulse. Assuming that the RC time constant of capacitor 470 with resistor 475 is long compared to the propagation delay length of tube 124, then potential in 470 will exhibit the expected first-order decay toward the load potential at 480 during the interval up to the next opening of valve channel 450. At the time of that next pulse, the voltage achieved to that point on 470 is again taken as a fixed potential for computing the net volume of the flow pulse.

With the model described, imagine that the pulse interval is just long enough for a pulse wave to travel the length of tube 124, reflect, and travel back to the proximal termination of the tube just at valve closure. Even imagining that the inductances of 440 and 460 are zero (to simplify the argument), if the wave impedance of tube 124 dominates the resistive load, it is possible to end up with pressure overshoot, that is, with enough charge transferred to capacitor 470 to raise its potential above that of capacitor 445. In effect, there is distributed inductance in the wave propagation model of the tube. Energy goes out of 445 to create momentum as the pulse wave travels in the distal direction of tube 124, and the reflected wave coming back proximally then stops that wave momentum and converts the kinetic energy of the wave to pressure expanding the tube, which ends up inflated along its entire length to a pressure exceeding the final pressure in 445. No energy conservation law has been violated. Energy has simply been transferred. In practice, some of that energy will be lost to viscoelastic damping in the tube material, but some of the kinetic energy will be preserved and transformed to pressure.

A substantial resistance at 475 can be advantageous for steady infusion. As the controller puts out a prescribed volumetric flow rate, a pressure potential quickly builds up in 470, i.e. compliant tube 124, to drive the controlled average flow into the load. Beyond the time of initial pressure buildup over a period on the order of R*C for R of 475 and C of 470, the accuracy of flow control will be unaffected. Head height variations in load pressure at 480 will not reverse the flow into the load except for a positive head height change exceeding the bias pressure differential established across resistance 475. Without a large resistance at 475, and especially in a very slow drug infusion, a head height change at the patient load could cause blood to flow backward into the compliance of tube 124, raising the possibility of clotting and clogging of the fluid path into the patient. Thus, resistor 475 has the effect of minimizing the sensitivity of short-term infusion rate to head height variations in 480. (In the long term, the controller imposes the prescribed infusion rate, so only short term effect involving charging or discharging capacitance 470 are of concern here.) When 475 is large, there is also a filtering action to smooth out the bumps due to flow pulses across 450. Hence, it is advantageous to use a flow restrictor at the distal termination of tube 124, making the resistance as high as possible short of preventing sufficient flow under conditions of maximum controller-requested flow and minimum driving pressure differential.

Another advantage of a substantial resistance at 475 is that a sudden complete loss of flow resistance from source 410 would not cause a near-instantaneous large infusion bolus, which could be harmful or fatal. With appropriate alarms, the fluid pathway could be clamped or otherwise interrupted before too much fluid passed to a patient. On the other hand, the redundancy of two normally-closed valves in the fluid path makes such a complete loss of flow regulation to "wide open" a very unlikely event. A large resistance at 475 is not essential to the proper functioning of the flow controller, which will adapt to achieve the prescribed flow regardless of load resistance, so long as sufficient pressure is available from the source to drive the prescribed quantity of fluid into the load.

Figure 5:
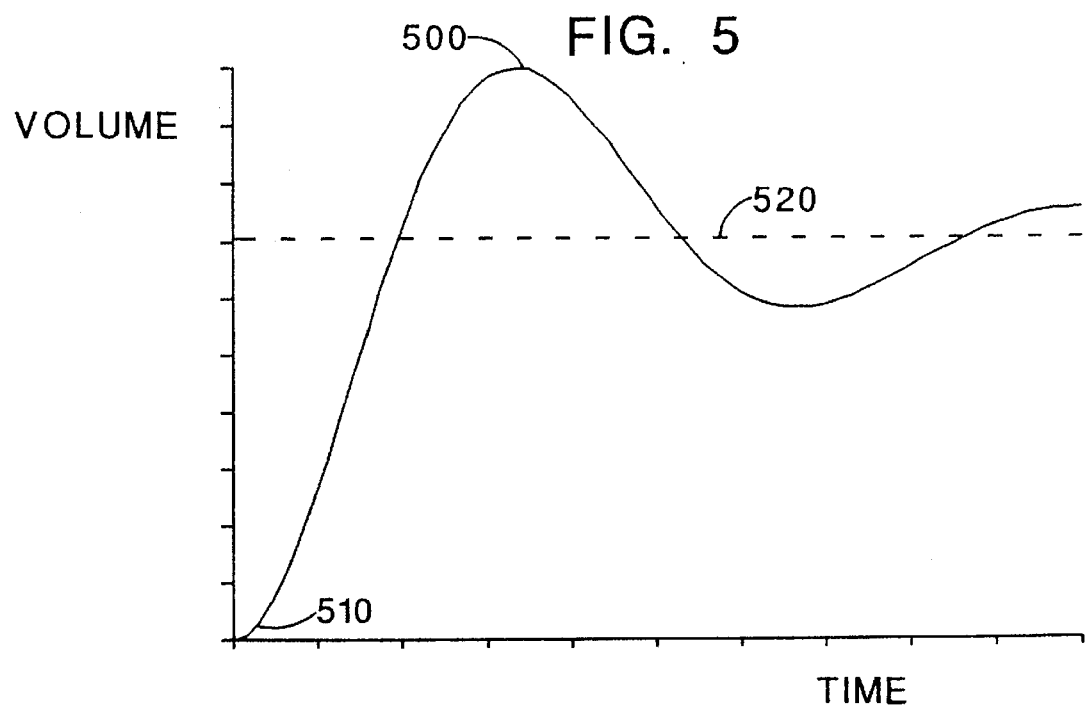
FIG. 5 illustrates fluid volume displacement versus time after valve opening, with indication of the fluid acceleration and fluid half-cycle timing regions utilized, respectively, for low and high volume flow rates.

Examining the dynamic characteristics of the circuit represented in FIG. 4, assume that only one of valves (transistors) 425 or 450 is open (on) at a given moment, so that the two sides of the circuit are decoupled. On the left, through 425, we have a series LCR circuit, where net inductance L is the sum of components 415 and 440 and net resistance R is the sum of components 420 and 435. On the right, as discussed, only series components 445, 440, 435, 460, and 465 count for flow pulse dynamics, leading again to a series LCR circuit model. After the flow pulse is over, the charge on 470 is adjusted for the flow pulse, and a first-order RC discharge is modeled into the load. The volume-versus-time response after opening either the proximal or distal control valve is represented qualitatively by FIG. 5, showing a damped sinusoid starting at zero slope at the instant of valve opening and oscillating about dashed equilibrium line 520. The volume change from the horizontal start of the volume curve up to the level of dashed line 520 is the product pressure-times-capacitance, for the pressure differential across the selected valve just before turn-on and the fluid capacitance of 445, the volume displacement sensor, which is the only capacitor in the short-time-constant dynamic model. It is entirely possible for the flow pulse response to become overdamped and exhibit no overshoot, depending on the design of the fluid path. At least a little overshoot is desirable in order to move a flow bolus quickly through the system and have the flow rate pass through zero, which provides an opportune moment to close the valve without any waterhammer and with minimal acoustic noise arising from the shutoff. In half-period timing mode, the valve-open time will therefore be set to give shutoff at point 500, right at the peak of the volume transfer curve. If flow impedances affecting cassette operation are not accurately known in advance in terms of controller algorithm coefficients, the controller will "experiment" with valve-open timing over a number of pulses to determine empirically the time interval to point 500, i.e. the time interval that maximizes the volume bolus. Note that the volume overshoot at 500 represents a pressure overshoot that will reverse the pressure bias in the check valve at closure. A valve like that represented in FIG. 2a could potentially leak in the "forward" direction of the valve regarded as a passive check valve, i.e. with flow from 115 down into region 205. A transient volume loss due to valve leakage of this sort will not cause harm, so long as the volume stabilizes for measurement of net displacement before the opposite valve opens to restore the normal bias direction to the valve that was tending to crack. The valve regurgitation will lessen the net bolus transfer size, most likely for working source-to-sink pressure differentials at the high end of the design range for the system, where a self-limiting of bolus size could even be beneficial by making maximum bolus size less sensitive to supply pressure.

Valve closure well past point 500 on the volume curve makes no sense, being wasteful of valve actuation power while achieving less than the volume transfer accomplished with a half-period pulse. Valve closure in the high-flow region before 500 is undesirable because of the waterhammer effect. Very early valve closure, e.g. at 510, early in the flow acceleration phase, can be used for variable control of small boluses with shutoff into a comparatively slow flow rate.

Design Formulas For Analyzing Dynamic Flow Performance

In order to obtain component values for the inductors, resistors, and capacitors of FIG. 4 or FIG. 12 (to be discussed later), the following design formulas are useful. Concerning symbols, special characters will be avoided in the following, as they have been above, in favor of strings of standard ASCII characters. The symbology can then be incorporated directly into ASCII variable names in computer code, as has been done to implement this analysis numerically.

In some texts the upper case letter "Q" is used to represent fluid flow rate, i.e. volume per unit time. Elsewhere, Q refers to the quality factor of a resonant circuit, the reciprocal of the dissipation factor. In electrical engineering and electronics, Q represents electric charge. In the following text, Q is taken, unconventionally, to represent fluid volume or, mnemonically, "Quantity." This fluid Q is conveniently analogous to charge Q in the electrical analog of the fluid circuits. The time derivative is often designated by a dot placed above the variable, but to avoid special characters, the character string D1Q will represent first derivative of Q with respect to time, i.e. flow, and D2Q will represent the second time derivative, i.e. fluid volume acceleration. P is pressure, analogous for voltage. The symbols L, R, and C are carried over directly from their electrical circuit meanings to their analogous fluid circuit meanings.

In the analysis that follows, a consistent use of SI units leads to correct results, with times in seconds, S, volumes in cubic meters, $M^3$, (not liters), masses in kilograms, Kg, densities in kilograms per cubic meter, $Kg*M^{-3}$, force in newtons, N, and pressure in pascals, $Pa=N*M^{-2}$. As earlier, "*" indicates multiplication. Note that the multiplier going from Q in $M^3$ to microliters is $10^9$ (not $10^6$). 1 Pa=6894.7 psi. Density RHO, for water=1000 $Kg*M^{-3}$, so going from specific gravity to density, multiply by 1000. Absolute viscosity MU, for water at 20 Celsius=0.001002 in SI units or 0.01002 Poise=1.002 Centipoise, in cgs units, so going from centipoise to SI units, multiply by 0.001.

Fluid inductance, L, resistance, R, and capacitance, C relate to pressure P and volume and its derivatives, Q, D1Q, and D2Q, as follows:

$$Q=P*C \qquad [7]$$

$$D1Q=P/R \qquad [8]$$

$$D2Q=P/L \qquad [9]$$

For steady laminar flow, fluid resistance R in a tube or radius r and length LGTH is given by:
$R=8*MU*LGTH/(PI*r^4)$ in the low-frequency limit For high-frequency oscillatory flow, where viscous shear forces affect only a negligibly thin fluid boundary layer, fluid inductance L in a tube of radius r is given by:

$$L=RHO*LGTH/(PI*r^2) \text{ in the high-frequency limit}$$

These formulas for R and L are not numbered, since they will be supplanted by frequency-dependent formulas. For rapidly accelerating flow, the boundary layer is thinner, viscous shear forces are therefore higher at the wall, and R is higher. A formula for boundary layer thickness THK with fluid oscillations at angular frequency OMEGA (not the same as OMEGA of Eq. 4) is useful for moving to an unsteady approximation for R:

$$THK=SQRT(MU/(2*OMEGA*RHO)) \qquad [10]$$

This thickness parameter has two dynamic applications: dissipation thickness, and displacement thickness. When fluid oscillates in a tube with a thin boundary layer near the wall, the inertia of the fluid column is increased as if the inside radius of the tube were reduced by THK, i.e. as if the boundary layer displaced the wall boundary inward by THK. Simultaneously, a fraction of the fluid moving in the tube is phase-shifted 90 degrees ahead of the acceleration-limited fluid, to the phase angle of resistance-limited fluid flow, flow which dissipates fluid power rather than storing the power in kinetic energy. This fraction, for thin boundary layers, represents the volume lying within a distance THK of the tube wall, i.e. the same volume that was removed as displacement thickness. Thus, THK represents dissipation thickness as well as displacement thickness.

For high-frequency oscillatory flow in a circular tube, where dissipation is confined to thickness THK between radius (r-THK) and radius r, the fraction of the flow cross-section shifted from "inductive" to "resistive" phase equals the dissipation factor, DF:

$$DF=2*THK/r \text{ in the limit as } THK<<r, \text{ i.e. the high-frequency limit}$$

Resistive impedance R in a series LCR circuit is related to inductive impedance OMEGA*L and dissipation factor DF by the formula:

$$R=DF*OMEGA*L$$

Fluid inductance L is increased as effective cross-section $PI*r^2$ is reduced by the factor (1−DF), raising L by the ratio (1+DF), asymptotically valid for DF<<1. As the boundary layer thickens with lowering frequency, the velocity profile settles into the limiting shape of a paraboloid going from twice the average cross-sectional velocity at the center to zero velocity at the tube wall. Looking at the kinetic energy in the flow in relation to the average velocity across the cross-section (i.e. that which multiplied by area gives flow rate D1Q), it works out that the energy is raised by the ratio 4/3, which implies that flow inductance L is 4/3 times the high-frequency limit value in the low-frequency limit.

The above considerations lead to high-and low-frequency asymptotes for L and R. While differential equation solutions are available to solve exactly for L and R at any arbitrary frequency, good approximations in simple formulas are given by blending the asymptotic formulas smoothly together, which leads to the following approximate engineering formulas:

$$R=\{8*MU*LGTH/(PI*r^4)\}*SQRT(1+(OMEGA*RHO*r^2/(32*MU))) \quad [11]$$

$$L=\{RHO*LGTH/(PI*r^2)\}/\{1-0.25/SQRT(1+(OMEGA*RHO*r^2/(32*MU)))\} \quad [12]$$

The low-frequency R and high-frequency L formulas will be recognized in the expressions in { ... } brackets immediately following the = sign. The correction factors that follow the { ... } brackets give, for R, the high-frequency asymptote and give, for L, both the asymptotic approach to the high-frequency limit and the low-frequency limit. Note that the term $OMEGA*RHO*r^2/(32*MU)$ is just the dimensionless ratio $((r/THK)^2)/64$. Capacitance C has to be derived explicitly from mechanical analysis of the spring shapes that make up the volume displacement sensor. This analysis, for the formed metal plate 330 of FIG. 3, is discussed in the referenced Measurement System Application.

Given an LCR circuit with complex roots, we obtain a real part RE to scale the envelope of exponential amplitude decay, and an imaginary part IM for the sinusoid angular frequency. We have:

$$RE=-R/(2*L) \quad [13]$$

$$IM=SQRT((1/(L*C))-RE^2) \quad [14]$$

Note that RE is negative and IM is positive. The damped sinusoid solution for time t elapsed, and with volume disequilibrium Q0 equal to capacitance C times the pressure differential initially across the valve, is given by:

$$Q=Q0*\{1-EXP(RE*t)*(COS(IM*t)-(RE/IM)*SIN(IM*t))\} \quad [15]$$

Note that if the SIN term were missing, the product of COS(IM*t) at zero initial slope times −EXP(RE*t) at positive slope gives a negative initial slope. The SIN(IM*t) term, whose coefficient is positive (since −RE is positive), offsets the negative slope to give a zero initial slope. This equation, for one particular damping factor, gives the waveform drawn in FIG. 5, where Q0 is the height from the start of the curve up to the dashed line.

It is to be noted that the approximations for L and R at frequency OMEGA actually apply to ongoing sinusoidal oscillations in flow, whereas the situation described here is flow acceleration starting abruptly from dead-stop and proceeding not into a sinusoid, but into a damped sinusoid. It has been determined that OMEGA should not be set to the angular frequency IM of Eq. 14 in order to obtain the best approximation for R and L because as damping rises toward critical, IM approaches zero, and yet the initial acceleration of flow at time zero is unaffected. In fact, we have acceleration:

$$D2Q=Q0/SQRT(L*C) \text{ at } t=0 \text{(i.e. at valve opening)independent of R}$$

Based on this observation, we define:

$$OMEGA=1/SQRT(L*C) \quad [16]$$

OMEGA is the undamped resonance frequency, and it is also the radius of the complex vector of components RE and IM, i.e.:

$$OMEGA=SQRT(RE^2+IM^2)$$

By this definition, OMEGA seems to be a good measure of fractional rate of change and is taken as the basis for estimates of R and C. Note that starting with a value for C, Eqs. 12 and 16 must be solved simultaneously for values of the variables OMEGA and L. This is readily accomplished iteratively by starting with OMEGA=0, solving Eq. 12 for L, plugging the result into Eq. 16 and solving for a new OMEGA, plugging this into Eq. 12 for a new L, etc. to convergence, which typically takes less than a half-dozen iterations to reach seven place convergence. With OMEGA defined consistent with L, Eq. 11 may be solved for R, followed by solution for RE, IM, and the function Q(t).

As described above, this form of solution can be applied to the flow pulse shape for pulsing of either the proximal or distal valves in the preferred embodiment of the controller, in general using different component values for L and R depending on which valve is pulsed, but with C remaining the same. To apply the analysis to the distal valve, 450, we still need a formula for estimating the contribution of wave impedance in tube 124 to resistance in 465. The following formulas are used in modeling of pulsatile flow in arteries. Representing pulse wave velocity in a tube as "c", using lower case to avoid confusion with upper case "C" for capacitance, we have:

$$c=SQRT\{(A/RHO)*(dP/dA)\}=SQRT\{(1/RHO)*(dP/dLN(A))\} \quad [17]$$

where area A is defined simply:

$$A=PI*r^2 \quad [18]$$

The second square root expression of Eq. 17 expresses simply that if area A is pulled into the denominator of the derivative of pressure, dP, with respect to area increment dA, one gets the denominator differential (dA)/A, which is the differential fractional change in area, or the differential of the natural logarithm of area, LN(A). If dP/dA is measured statically or at low frequency with a tube whose wall material exhibits creep, e.g., PVC tube, then the value obtained will be lower than for the frequency range of pulse wave propagation in the current context. The derivative dP/dA is always an increasing function of frequency in lossy polymer materials, and the higher the dissipation of the material, the steeper the frequency slope. Propagation velocity c can be measured empirically by abruptly opening a valve at one end of a tube sample and measuring the time delay to 50% of the peak pressure change at the closed distal end (noting that the peak pressure change will generally exceed the pressure change after settling, due to the effect of wave reflection.) Creep or viscoelasticity will also cause waveform dispersion, so that a sharp propagating wavefront will not be observable when a pulse comes along, but the analysis given here will continue to give the correct approximate magnitude for flow impedance at the entrance to tube 124:

$$R=(RHO/A)*c=SQRT\{(RHO/A)*(dP/dA)\} \quad [19]$$

The first form of the equation is the most useful if velocity c is measured empirically, which is likely to give the best results for pulse characteristics. The important issue is to determine whether the magnitude of R is going to be large enough to cause overdamping of the flow pulse through valve 450. If there is overdamping and a controller algorithm is extending a pulse interval seeking a maximum bolus volume, the pulse interval will be stretched out to the point where a return wave reflection reverses the volume flow into tube 124, which may be too long to wait if solenoid power is being consumed. It may prove practical to work with an overdamped output pulse, in which case the pulse duration for large boluses should be limited to some interval of diminishing volume returns for the actuator energy investment. (If a piezoelectric valve actuator is used, the energy conservation question is moot, since holding charge on the actuator capacitance does not use power.)

The analytic solutions and techniques presented above, along with the RC first-order decay solution for flow into the load after a pressure pulse, yield an adequate model for designing this system and its controls to meet a given application. Below, a particular method of algorithmic control is described, based on the analysis just given. Variations on the theme presented will be readily apparent.

A Method For Average Flow Control In The Preferred Embodiment

Figure 6:
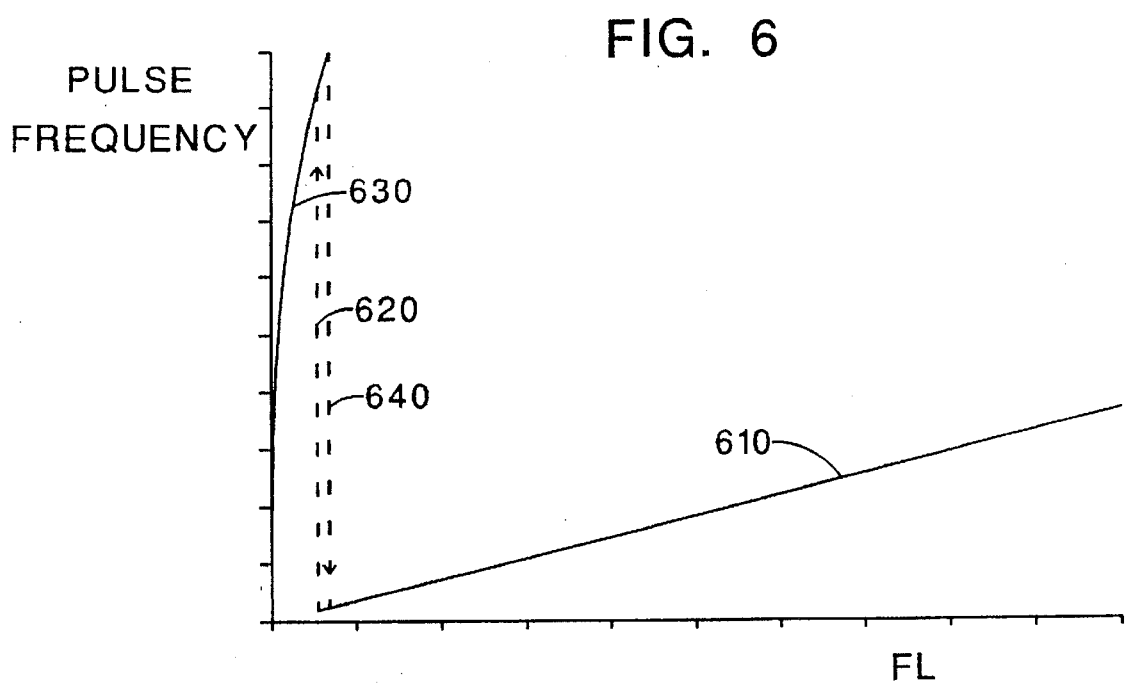
FIG. 6 illustrates valve pulse frequency as a function of a linear rate-controlling parameter of the flow control system, including hysteresis in the transition between acceleration and half-cycle timing modes.

The graphs of FIGS. 6, 7, and 8 are interrelated and all derive their significance from the VOLUME versus TIME graph already discussed in relation to FIG. 5. As with previous figures, the leading digit of three (or for FIGS. 10 and above, the leading two digits of four) of a label number indicates a figure number in which the labeled item appears. Thus, repetitions of figure numbers with label numbers are not necessary.

In FIGS. 6, 7, and 8, "FL" is a non-dimensional parameter that controls flow. Actual flow rate is nearly linear with FL, provided that the flow control algorithm coefficients are matched to the time constants and damping factors of the fluid delivery system. Q.NET is defined as total measured infused volume, whose graph against time will be a stairstep function incremented at each infused bolus. One can define the volume derivative, FLOW, not as an instantaneous slope, but as slope over a period of one pulse stairstep:

$$FLOW=delta(Q.NET)/delta(TIME) \text{ over one pulse period} \quad (20)$$

Volume/Time rate FLOW depends on control parameter FL multiplied by the difference between source pressure P.SOURCE and sink pressure P.SINK and further multiplied by a system flow scaling coefficient KF according to the equation:

$$FLOW=KF*FL*(P.SOURCE-P.SINK) \quad [21]$$

Eq .21 is solved for FL:

$$FL=FLOW/\{KF*(P.SOURCE-P.SINK)\} \quad [22]$$

and the resulting parameter FL is applied to the control algorithm that sets pulse frequencies and widths for the proximal and distal valves. The coefficients for getting from FL to those pulse frequencies and widths are adjusted dynamically so that Eq. 20 is satisfied. That is, FLOW as a controller target is used to compute FL, then FL sets pulse widths and frequencies, and the result is to cause a measurable delta(Q.NET) that is used to solve Eq. 20 for achieved FLOW. To the extent that achieved FLOW misses the target value of FLOW used in Eq. 22 to compute FL, the coefficients going from FL to pulse control parameters are adjusted. The coefficient KF is not adjusted, but is simply for convenience of scaling the numerical range of FL, e.g., so that FL runs nominally from 0 to 1 to cause flow to vary between 0 and the maximum rated throughput for the system.

In FIG. 6, pulse frequency is graphed as a function of parameter FL. In linear region 610 of pulse frequency, pulse width 710 (FIG. 7) is kept constant, which keeps pulse volume 810 (FIG. 8) constant except for possible variations due to head height changes. The pulse width in this region is adjusted to approximate point 500 (FIG. 5) of maximum volume transfer unless, in an overdamped system, valve closure is imposed before flow completely stops. The result of a linear variation in frequency at constant pulse volume is a linear variation in FLOW. At the left end or region 610, pulse frequency reaches a lower limit, below which more frequent pulses are needed for flow continuity. This limit may be on the order of 0.05 per second (three per minute), or possibly smaller if a large termination flow resistance 475, in conjunction with a comparatively large tube compliance capacitance in 470, yields adequate smoothing of the flow boluses.

At the lower limit of FL, there is a discontinuous change in operating mode, as indicated by dashed lines 620, 720, and 820 with directional arrows. Pulse frequency jumps up (620) while pulse width jumps down (720), causing pulse volume (820) to jump down by a much larger ratio. The operating point has moved on the VOLUME/TIME graph from 500 to the vicinity of 510, in early flow acceleration. In this region, labeled by 630, 730, and 830, pulse volume varies nearly as the square of pulse width, which gives larger fractional changes in pulse volume than occur in pulse width. In a preferred flow control method, both pulse frequency and width vary as the cube root of FL in the variable-bolus region. The square-law dependence of bolus volume on pulse width yields flow control linear with FL. This method could be likened to programmed shutter speed and aperture combinations on film cameras, where the net exposure is controlled over a much wider dynamic range than is used in either shutter speed or aperture. Obviously, dependencies of pulse width and frequency other than the cube root of FL can be used to achieve linear control, as long as the product of bolus volume and frequency is controlled properly. As FL varies in the variable-bolus region, it can rise above the transition point to the variable-bolus mode. At some point above the first transition is a second transition, 640, 740, and 840, back to the fixed-maximum-bolus mode. By providing hysteresis between the two transitions, controller jitter is avoided. This is important, especially from the perspective of noise annoyance. Although the controller is not inherently noisy, it is difficult to engineer the design to be completely inaudible under all conditions. In a quiet room with the controller near a patient without hearing impairment, the controller pulses are likely to be audible. If their rhythm is regular, like ticks of a clock, the pulse sounds will be readily ignored. If the rhythm jumps from slow to fast or fast to slow, probably accompanied by a change in sound quality because of the pulse interval change, attention will be called immediately to the noise.

Figure 9:
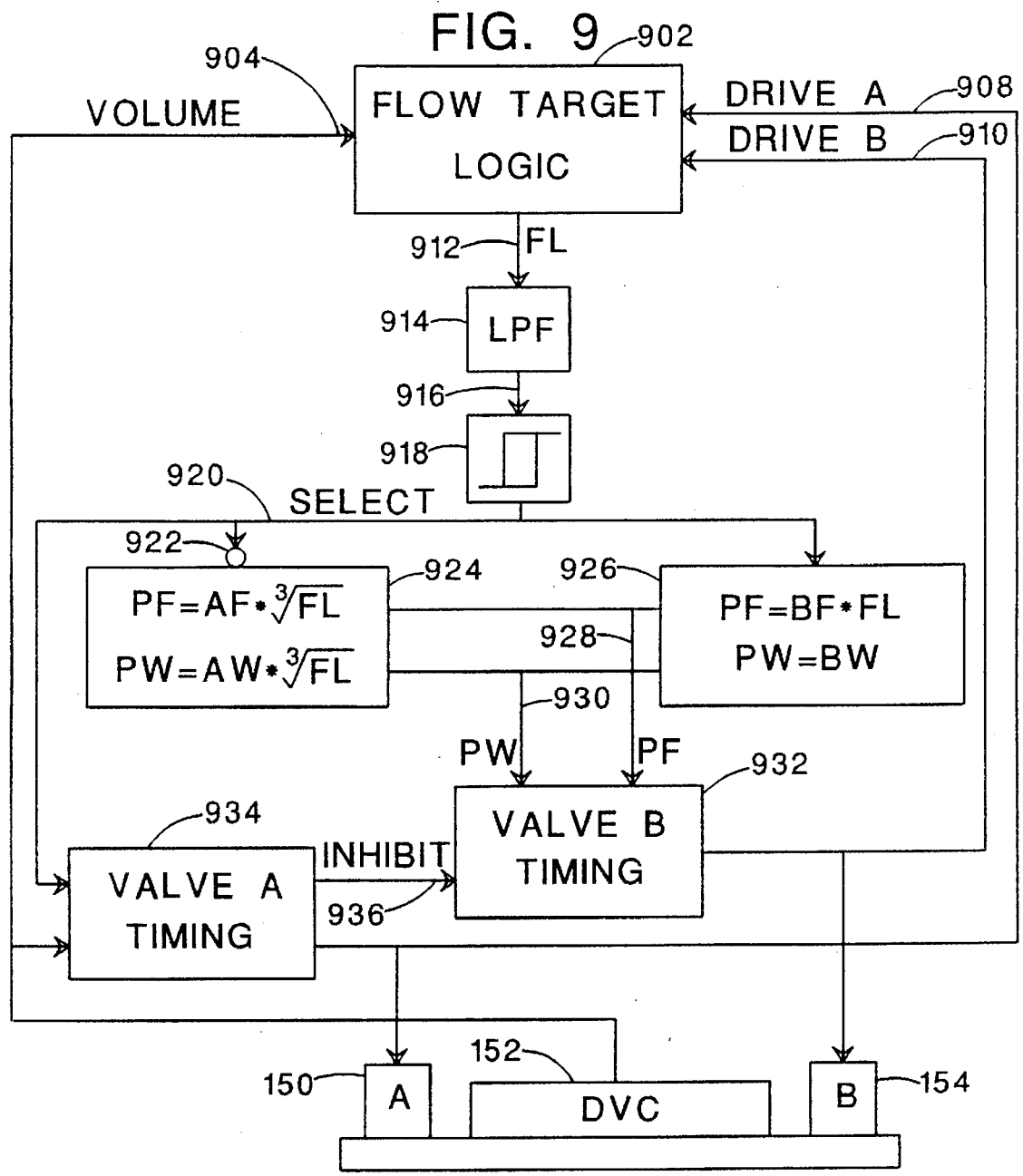
FIG. 9 illustrates, in an overview block diagram, the control software method for regulating flow to track a volume target line over time.

The hysteresis control just described is further detailed in reference to FIG. 9, which is a functional block diagram for a preferred controller method. Each block represents a software module which receives input parameters, performs computations, and delivers output parameters. In many instances, the timings as well as the values of input and output parameters are of significance, i.e. the parameters are of a dynamic nature for real time control. The "FLOW TARGET LOGIC" module 902 computes the flow control parameter "FL" based on a moving target for delivered volume, interpreted in relation to "VOLUME" sensor inputs via 904 from Direct Volume Converter "DVC" 152 (of FIG. 9, first seen in FIG. 1a), along with valve timing inputs "DRIVE A" at 908 and "DRIVE B" at 910, the signals that control the energization times of the actuators for proximal valve "A" at 150 (first seen in FIG. 1, here viewed as a block of FIG. 9) and distal valve "B" at 154 (FIG. 9, again first seen in FIG. 1). The output parameter FL of 902 is passed via path 912 to digital low-pass filter module 914, "LPF", which takes part in avoiding jitter between operating modes. The output parameter of 914, a filtered version of the continuous (within the resolution of the digital representation) variable FL, is passed via path 916 to hysteresis module 918, whose output is binary parameter "SELECT" on 920. 918 compares its input from 916 to upper and lower threshold values and sets "SELECT" to "TRUE" whenever the input exceeds the upper threshold, and to "FALSE" whenever the input falls below the lower threshold. A graph of "SELECT" against input 916 shows a hysteresis loop, as indicated by the shape diagrammed in box 918. The combination of low-pass filtering and threshold hysteresis avoids jitter between operating modes, as described above. "SELECT" on 920 is applied directly to module 926, and inverted to module 924, where circle 922 at the input to 924 indicates logic inversion. Thus, when select is "TRUE" then module 926 is selected and 924 is deselected, and vice versa, "FALSE" selects 924 and deselects 926. Module 926 represents the choice of Pulse Frequency "PF" and Pulse Width "PW" in fixed maximum bolus mode, Mode B, with the bolus volume target and corresponding pulse interval time represented at point 500. The width coefficient "BW" is adjusted to achieve this peak volume at 500 and is the height of line 710. The frequency coefficient "BF" is the slope of line 610 and is chosen for the range of frequencies appropriate to the mechanical and fluidic design with its range of source pressures and rate targets. Module 924 represents the choice of "PF" and "PW" in variable bolus mode, Mode A. As discussed earlier, PF and PW are set proportional to the cube root of FL with frequency scaling coefficient "AF" to give "PF" and width scaling coefficient "AW" to give "PW". The resulting PF curve is 630, and the resulting PW curve is 730. The values of "AF" and "AW" are chosen in relation to "BF" and "BW" and a best estimate of the shape of the VOLUME(TIME) function curve of FIG. 5 to achieve matched flow rates for matching values of "FL" going into the two algorithms. While maintaining this match, the ratio of "AF" to "AW" is adjusted to achieve a practical combination of pulse width range and pulse frequency range. After initialization, the values of "AW" and "BW" are subsequently corrected, in the course of control, to maintain a fixed calibrated relationship between "FL" and measured volumetric flow rate. Note that the value for parameter "FL" appearing in modules 924 and 926 is updated with each new computation of "FL" at module 902, whereas the parameter "SELECT" via 920 results from processing of "FL" as described.

The selected one of modules 924 and 926 provides output parameters PF and PW via paths 928 and 930 to "VALVE B TIMING" module 932. This module provides the real-time binary control signal "DRIVE B" on 910, Whose pulse width and pulse frequency control timing of the power driver circuit for valve assembly "B" at 154. The signal on 910 also provides synchronization to "FLOW TARGET LOGIC" module 902 for determining when to read volumes for computation of net delivered volume.

While "VALVE B TIMING" at 932 seeks to maintain a prescribed flow rate out to fluid "LOAD" 480, via feedback through, ugh the "FLOW TARGET LOGIC" at 902, the software module "VALVE A TIMING" at 934 operates only in maximum fixed bolus mode and functions only to replenish the volume in fluid capacitance 445, which is the volume sensed in "DVC" 152, whenever that volume becomes too depleted. Hence, 934 monitors the parameter "VOLUME" from 152 via path 904 to its input, and activates whenever "VOLUME" falls below a prescribed threshold. That threshold depends on the operating mode indicated by the input "SELECT" via 920 from 918, and depends upon an estimate from "FLOW TARGET LOGIC" 902 of the pressure span from the fluid source to the fluid load at tube 124. In maximum-bolus mode B for valve B, 934 is set to fire a pulse to 150 via output 908 whenever valve B at 154 fires and depletes the volume sensed in 152. This firing is delayed by a short latency interval to allow for an accurate volume reading but is more or less immediate, so that the fluid reservoir of 152 is waiting full and ready for the next output pulse. In variable-bolus mode A for valve B, as indicated when "SELECT" on 920 is "FALSE", the volume threshold for 934 is set toward the center of the available operating pressure range from source to sink. This setting, which varies the volume bias at which 152 senses, may be fixed or varied at will. A high setting results in more frequent pulses of valve A at 150, less frequent pulses of valve B at 154, less fractional variation in pressure in 470, and consequently less fractional variation in pulse frequency PF.

Figure 10:
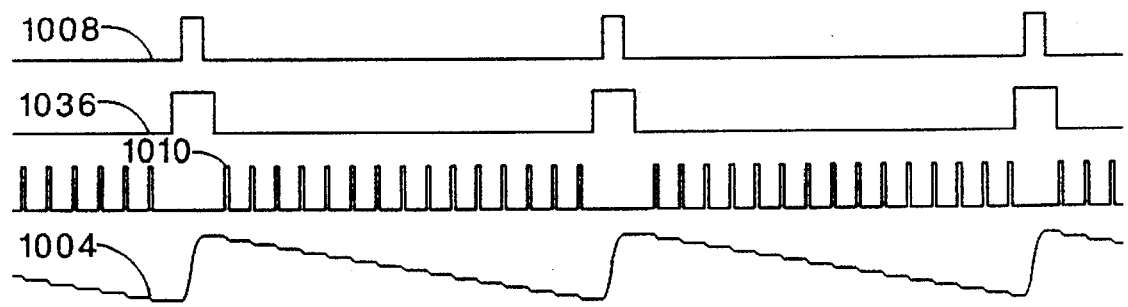
FIG. 10 illustrates upstream and downstream valve pulse timings in relation to sensor volume changes in a hybrid operating mode, with infrequent maximum boluses from the source and frequent small boluses to the sink.

The relationships described here are better understood with reference to the timing diagram of FIG. 10. The declining "VOLUME" signal on 904 is indicated by curve 1004, which declines in small increments with each pulse to valve B on 910, indicated by pulse train 1010. When 1004 reaches a minimum threshold, it triggers the logic in 934, whose immediate response is to set "INHIBIT" to "TRUE", where "INHIBIT" is the parameter being passed symbolically via 936 from 934 to 932. The signal on 936 is graphed against time as 1036. After a time delay for highly accurate volume determination, e.g., averaging over a longer-than-usual interval to obtain precision and resolution, valve A activation signal 908 pulses high and low, as plotted against time on curve 1008, giving a maximum-bolus interval. Volume on 1004 swings up through a half-period of the damped sinusoid of FIG. 5 and is stopped by valve closure at the top. An interval elapses after valve closure for a second highly accurate volume determination, following which "INHIBIT" signal 936 as shown on trace 1036 goes low, i.e. "FALSE", and valve B pulsing is allowed to resume, causing volume on 1004 to descend by small steps. Not visible on the scale of FIG. 10, the descending steps of curve 1004 are downward curving parabolas, starting from horizontal tangency and bending downward until the descent is interrupted abruptly by valve closure. The accurate volume determinations in the inhibit intervals just before and just after the pulses of 1008 are used to track the total volume delivered to the fluid sink. Intermediate volume determinations are not critical for accuracy, being used just for control monitoring.

While FIG. 10 is correct for the above qualitative description, the time scale of the features has been distorted for clarity of illustration. In actual practice, the widths of pulse-high intervals of traces 1008, 1036, and 1010 are much narrower in relation to the time baseline, which causes the transitions in graph 1004 to be correspondingly steeper, appearing vertical on the time scale drawn. For example, the variable-bolus pulses of trace 1010 could be of the order of three milliseconds wide and spaced at one second intervals, implying a high-state duty cycle of 0.003. The interval between maximum-bolus pulses on 1008, spanning about 15 pulses on 1010, becomes about 15 seconds. The pulse width on 1008 could be of the order of thirty milliseconds. The high-state duty cycle on. 1008 would then become 0.002. On this time scale, the S-shape of the volume rise on 1004 would not be visible. The width of pulses on trace 1036 in excess of the pulses on 1008 might be on the order of fifty milliseconds extra before and again after the pulse on 1008, to allow for settling of transient vibrations and a frequency count interval of perhaps ten milliseconds. This pushes the pulse widths on 1036 up to 130 milliseconds, which fits well within the pulse interval for the pulse train of trace 1010. Thus, in a typical context for this invention, the refill pulses of 1008 and the surrounding inhibit intervals of 1036 could fit into latency intervals between pulses of 1010, giving an uninterrupted rhythm of output pulses, with (e.g.) every fifteenth pulse sounding a little different because two events, an input pulse and an output pulse, fall within a 100 millisecond interval and are barely resolved by the ear as separate events.

"FLOW TARGET LOGIC" module 902, monitoring curve 1004, infers from the volume reading the associated pressure, and infers from the volume increment sizes what the fluid load pressure has to be, consistent with the known flow dynamic characteristics of the controller. From the resulting inference of pressure differential between fluid capacitors 445 and 470, 902 adjusts parameter FL dynamically to achieve constant fluid boluses, applying Eq. 22. Thus, the pulse frequency and width of 1010 will become larger as the volume reading on 1004 descends, and frequency and width will shrink again as 1004 jumps back up. (This corrective variation in frequency and width is not shown in trace 1010.) The variations in the measured volume boluses as 1004 descends will indicate to 902 any error in its estimate of load pressure in relation to the pressure derived from the PRESSURE(VOLUME) calibration curve of sensor 152. The volume jumps monitored during pulses to valve A will indicate the source pressure. Based on this information about source and load pressures, 902 has the information necessary, among other things, to adjust the threshold used for "VALVE A TIMING" at 934 in relation to source and load pressures. Another monitoring function accomplished by source and load pressure estimation is determination whether source and load pressures are within normal operating ranges. A depleted source or a clogged fluid path in the load will be readily apparent from these data, and an alarm can be triggered if operator intervention is required.

At the highest level of control, the function of the "FLOW TARGET LOGIC" module 902 is to take a target net volume, V.T, which moves with time at an associated target volume rate D1V.T, and cause the net delivered volume stairstep function Q.NET and its one-cycle slope, FLOW, to close simultaneously with the targets V.T and D1V.T. The tool to accomplish this is Eq. 22 for setting control parameter FL, along with a rate-setting equation such as the following:

$$FLOW=D1V.T+(V.T-Q.NET)/TAU \quad [23]$$

As a procedure rather than an algebraic identity, Eq. 23 assigns a value to FLOW according to past volume delivery performance, then Eq. 22 assigns a value to control parameter FL based on FLOW and estimated pressure conditions.

"TAU" is a time constant controlling system convergence. If TAU is set to the current pulse period, the effect will be to correct the error (V.T−Q.NET) in a single pulse step. Setting TAU any shorter will cause overcorrection and possibly instability. Setting TAU longer than the minimum will prevent the system from jittering and over-responding to external variations such as "noise" variations or pulsations in load pressure. If TAU is extended to well over one pulse period, the implementation of Eq. 23 will cause volume error to decay over time with a time constant of approximately TAU. Implicit in Eqs. 22 and 23 is an ongoing correction of the parameters that translate from FL to pulse frequencies and widths: AF, AW, BF, and BW, as appearing in 924 and 926 of FIG. 9. In the preferred embodiment, AF and BF are left constant while AW and BW are adjusted to calibrate FLOW in the two operating modes. An alternative operating mode is noted here, useful for very slow infusion. If the outgoing volume pulses via 154 need to be kept very small, this can be accomplished with a larger, more manageable pulse width if the fluid source at 152 is maintained at a pressure bias not much above that of the fluid load. This can be accomplished if the refill pulses to 150 are not maximum-bolus pulses, but much shorter pulses, in the flow acceleration phase. Then 152 is not "topped up" each time, but held to a low bias pressure. The timing diagram of FIG. 10 still applies in this case, qualitatively, except that the refill volume boluses are kept small, and the shape of the rising segments of 1004 is upward-curving parabolas chopped off at valve closure time, rather than S-shaped curves going smoothly to horizontal tangents at the top.

In the event that either valve 150 or 154 fails to close, e.g., because of a particle lodging and unseating disk 210 or its counterpart in valve 120, the flow controller of the present system will immediately recognize the failure and will be able to maintain ongoing controlled infusion, although with a possible loss of accuracy. The system should be programmed to set off a malfunction alarm even as it continues operation, since redundancy in the system will be lost and the reliability of continued operation put in question. As long as initial operation has been normal, the controller will have derived flow control coefficients AF, AW, PF, and PW, that in conjunction with a good pressure differential estimate lead to a calibrated infusion rate using output valve B alone. Similar parameters will have been derived for input valve A. The net effect of system geometry and fluid properties is thus self-calibrated and the resulting coefficients available for open-loop control.

If source valve 150 fails open, the pressure proximal to sink valve 154 will rise to the source pressure, a situation immediately recognized by the controller. The controller will further have a good estimate of the difference between this source pressure and the load pressure, as well as an indication of the relationship between pulse width and pulse volume in the form of the adjusted flow control coefficients. The controller can therefore continue to pulse, open loop, delivering a comparatively accurate volumetric output to the sink, even though volume-change feedback data are no longer available. If the source supply becomes depleted, this will be measured directly by a drop in pressure at 152. If the fluid path to the sink becomes closed, then pulsing of valve 154 will cease to produce transient ripples in the output of 152, and the controller will know that flow has been interrupted.

If sink valve 154 fails open, the pressure distal to source valve 150 will fall to the load pressure, again an immediately recognizable situation for the controller. Guessing that the source pressure is maintained constant and with constant monitoring data on load pressure, the controller has a sufficient description of pulse width versus bolus volume characteristics of the source to maintain regulated flow. Pinching off of the fluid path to the sink will result in a readily observable rise in the volume signal from 152. Loss of, source fluid will result in disappearance of the transient ripples from 152 that should normally accompany pulses from the source.

DETAILED DESCRIPTION OF A SECOND EMBODIMENT

The system described above; uses two valves to permit accurate volume readings at zero instantaneous flow rate, giving an indication of total delivered volume. Two valves are not always necessary to the proper functioning of the invention, especially if the system need not function over an extremely wide dynamic range of precisely monitored rates. The failure mode described just above, for sink valve 154 stuck open, suggests a design that can regulate flow to a sink with just one valve. By adding a flow restrictor just distal to the volume displacement sensor, a dynamic is obtained in which on-the-fly volume readings can be interpreted to derive an accurate measurement of fluid flow to the load. A substantial downstream flow resistor adds safety, should the one valve in this second embodiment fail in an open state: there will not be a sudden rush of fluid to the output. The flow restrictor will passively slow the flow rate while an alarm sounds, giving time for an operator or the patient to intervene and prevent over-infusion.

Figure 11:
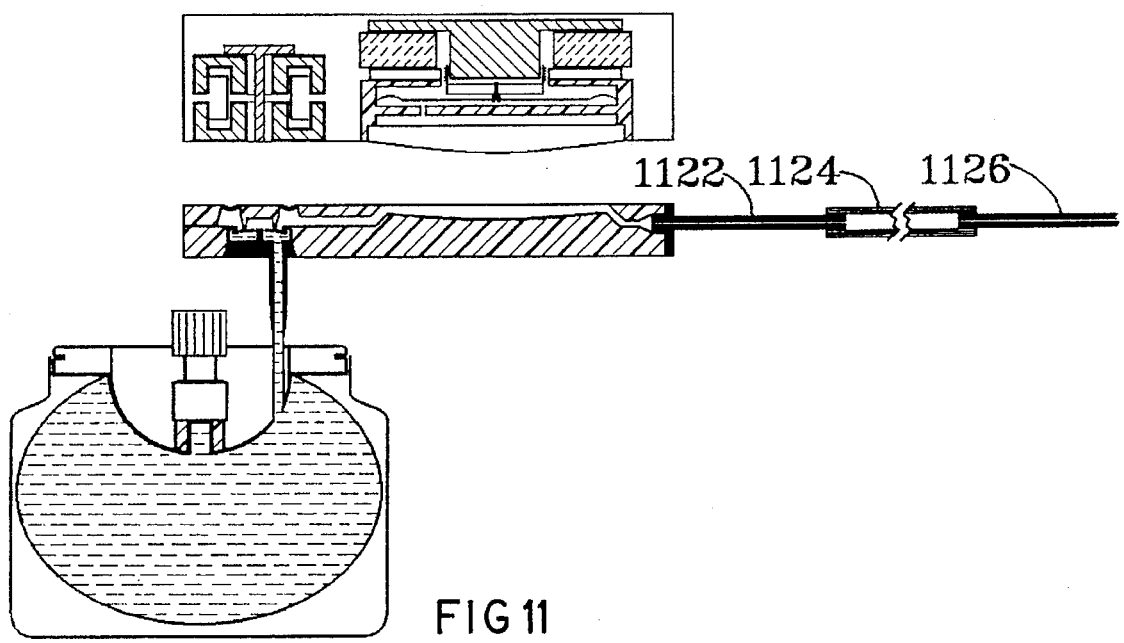
FIG. 11 illustrates the single-valve, downstream flow restrictor embodiment of the system.

Examining FIG. 11, all the components and their functions are analogous to FIG. 1a up to fluid path 118 from the volume displacement interface chamber, and up to valve actuator 154, which is eliminated. Valve opening/closing component 120 and path 122 are gone. In place of paths 118 and 122, which are of relatively large diameter and intended to function as fluid inductors, the system has flow restrictor 1122, larger tube 1124, and distal flow restrictor 1126. Of these, 1122 has a similar function to series restrictive pathways 118 and 122, except in this case 1122 is a much smaller bore and is intended as a resistive flow restrictor, ideally with a fairly large inductance as well. A high-quality inductor is not sought in 1122. FIG. 11 suggests that 1122 is a segment of microbore tubing. A pinhole restrictor could be used but may be less desirable, lacking the inductive impedance component that can be helpful in obtaining accurate dynamic volume readings. Tube 1124 is functionally no different than tube 124 except that there is no advantage to low pulse wave impedance, so 1124 can be, a small tube. Tube 1126 functions no differently than optional tube 126 of the preferred embodiment, which was discussed above.

It is noted that two separate flow restrictors are incorporated into the second embodiment, one at either end of fluid delivery tube 1124, for the following reason. The proximal flow restrictor, 1122, provides the flow inertia, or inductance, to prevent abrupt changes in flow rate out of the volume sensor when an inlet pulse is applied to that sensor. The way this imposed sluggishness in flow rate change is used in volumetric delivery computation is described below. Connection of the sensor discharge directly to a larger tube, e.g. tube 1124, would give rise to a short-term resistive load, associated with compliance and related wave impedance of the tube. With the loss of inductance would go a loss of continuity in the first derivative of volume, making it more difficult to extrapolate outgoing flow into the valve-pulse region. Distal flow restrictor 1126 serves the same function described for 126 in the preferred embodiment—to smooth out flow pulses and avoid temporary flow reversal with change of head height. If tube 1124 is made small and of low volumetric compliance, then restrictor 1126 becomes less critical and might be omitted. Similarly, a small and not very volume-compliant tube 1124 will offer a high resistive impedance to short pulses, making estimation of delivered volumes less difficult even if restrictor 1122 is omitted. Hence, the design could be made to function well with a small low-compliance tube set and no additional flow restrictors.

Figure 12:
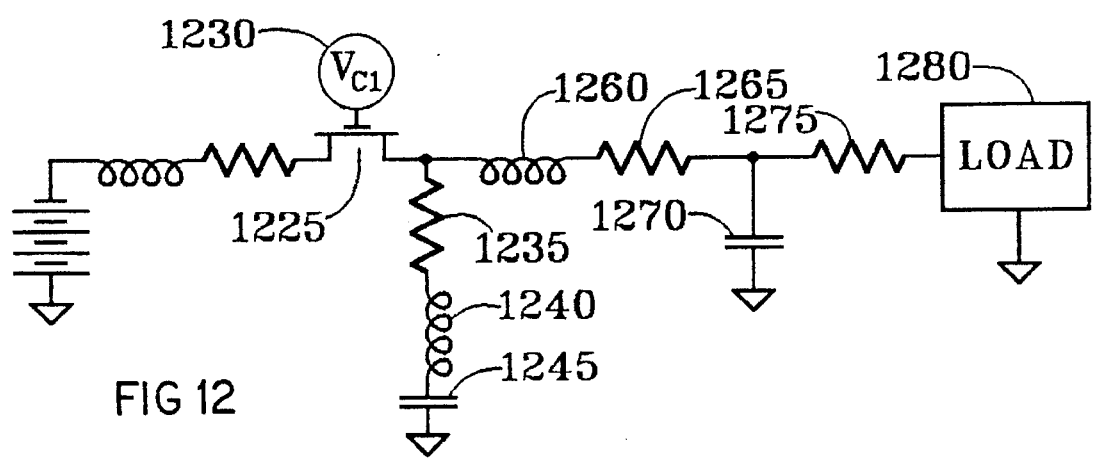
FIG. 12 shows an electronic circuit schematic analogue of fluid flow dynamics in the controller of FIG. 11.

The dynamic flow characteristics of the second embodiment are illustrated by schematic FIG. 12, which is analogous to FIG. 4 in all components except for valve path 450 and associated control 455, which are replaced by a direct fluid connection. Fluid path 1225 with control 1230 are analogous to 425 and 430, and capacitor-inductor-resistor combination 1245-1240-1235 (respectively) is analogous to the 445-440-435 combination, but the junction of 1225 and 1235 connects directly to inductor 1260, which is analogous to 460, without the intervention of a valve analogous to 450. Quantitatively, inductor 1260 is substantially larger than 460, and resistor 1265 is very much larger than 465, by design. Tube capacitance 1270 is analogous to 470 but might be quantitatively much smaller if a small tube is used, as is allowable in the system context of this second embodiment. 1275 is analogous to 475 but might be larger, since this second embodiment will generally not handle the high flow rates of the first embodiment and can therefore tolerate higher-resistance flow restrictors. Load 1280 is analogous to load 480.

Figure 13:
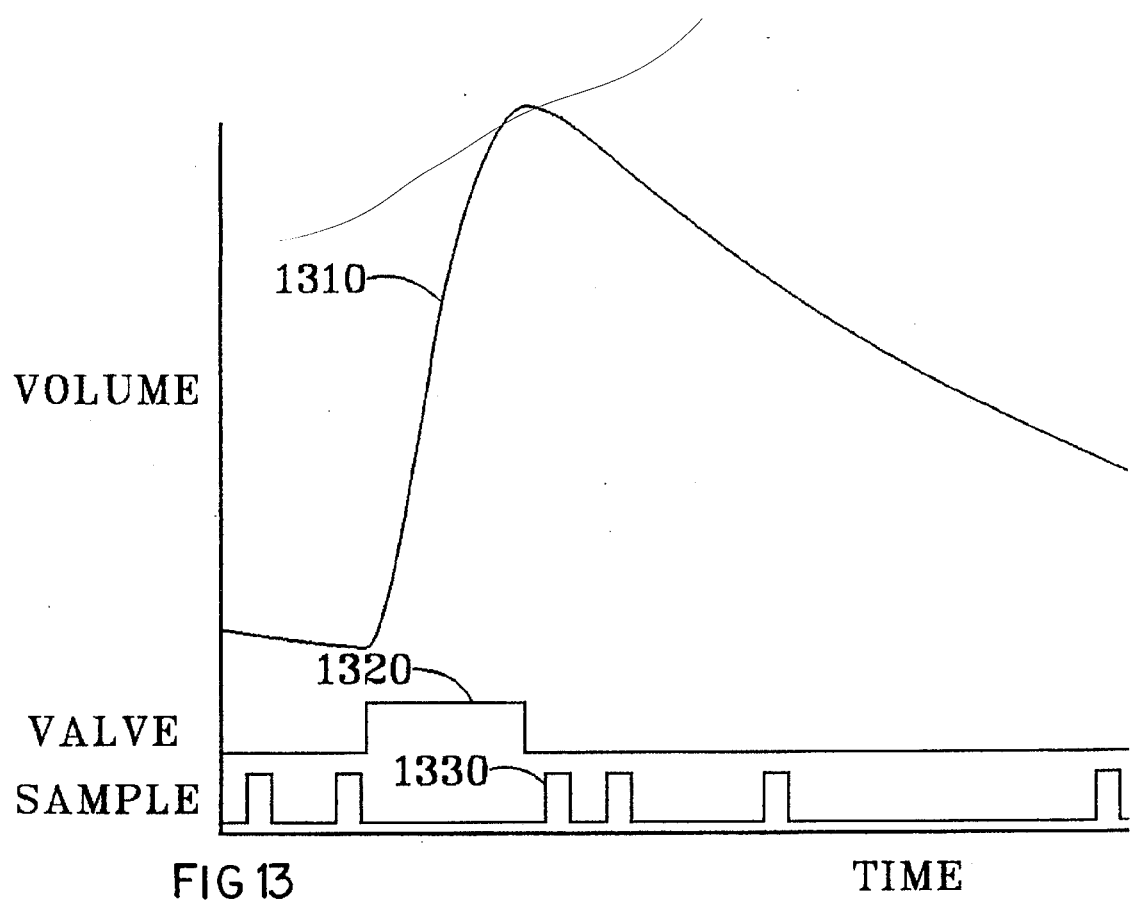
FIG. 13 illustrates a maximum-bolus flow pulse with valve timing and volume sample timing for the system of FIGS. 11 and 12.
Figure 14:
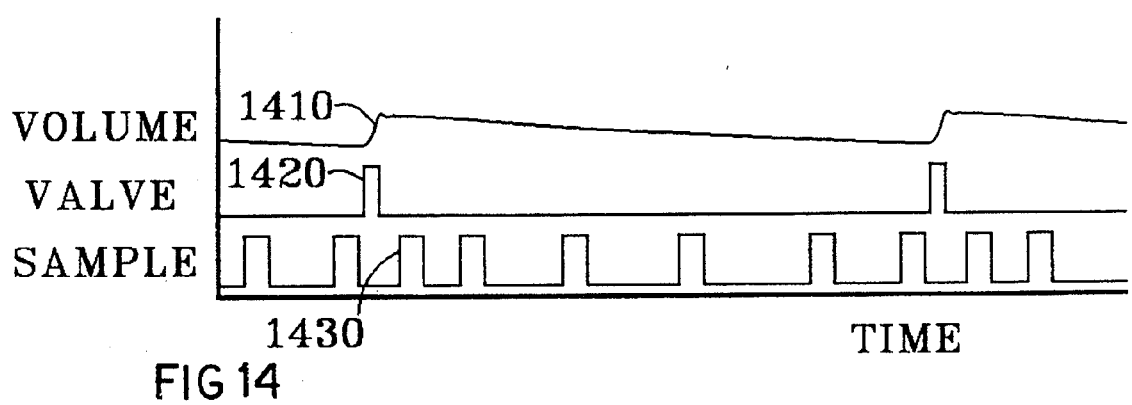
FIG. 14 illustrates a small-bolus flow pulse with valve timing and volume sample timing, analogous to the maximum-bolus traces of FIG. 13.

The dynamics of the single-valve system of FIGS. 11 and 12 are illustrated in FIG. 13. for a maximum bolus and in FIG. 14 for a small variable bolus. The features in the two figures, though different in valve timing and volume magnitude, arise from the same fluid dynamic time constants derived from the schematic in FIG. 12. The horizontal axes for FIGS. 13 and 14 are time. Looking first at FIG. 13, volume trace 1310, the volume sensed between valve 1225 and outlet inductor 1260, responds to the valve-open pulse-high interval illustrated on trace 1320. Just before 1320 pulses high, 1310 is sloping down, following an exponential decay curve of fluid volume discharge. When 1320 goes high, fluid flow from valve 1225 accelerates and then decelerates to zero rate at the valve closure point where 1320 goes low, following a curve like that of FIG. 5 from the beginning up to the point labeled 500. During this volume increase interval, fluid flow out of the volume sensor area via inductor 1260 and resistor 1265 is accelerating in response to the increasing pressure at the junction of 1260, 1225, and 1235. Thus, by the time valve 1225 closes, the downward slope of trace 1310 has become steeper than before the recharge pulse. With continuing flow acceleration, 1310 continues to bend downward but soon goes through an inflection and settles into an exponential decay curve asymptotic to a limit-volume determined by pressure in the load. Pulse wave action in tube segment 1124 may in some embodiments cause further visible wiggles in the shape of trace 1310. The important point here is that there is always a flow going out of sensor capacitance 1245 via 1260 and 1265, and during valve-open pulses, this flow is superimposed on incoming flow in the measurable sensor reading. Further, using the volume-to-frequency conversion method that has been described above, the volume reading on 1245 cannot be sensed instantaneously or nearly so, but only over a count interval, typically of more than one and up to several milliseconds duration to obtain high resolution. Thus, the volume readings are smeared over the pulse-high intervals illustrated in trace 1330, labeled "SAMPLE". The controller must infer the net volume delivered to the load from these data using algorithms that take account of the dynamic nature of the measured fluid flow and the volume sensing process.

As with FIG. 10, the time scale of FIGS. 13 and 14 has been distorted for illustrative clarity. The valve-open pulse of FIG. 13 is typically of the order of thirty milliseconds, while the interval to, the next pulse is typically of the order of one second. Thus, the volume decay curve of trace 1310 is not nearly as steep, in proportion to the volume increase, as is illustrated. This means that accuracy of the dynamic representation is not as critical to overall volumetric determination as would be suggested from the waveform shapes of FIGS. 13 and 14.

Continuing to examine FIG. 13, the pulses on trace 1330 indicate that two volume samples are taken before the recharge pulse, and four after, the latter four starting immediately after valve closure and being spaced by increasing time delay intervals. The two pulses before the recharge pulse determine a volume and volume slope, establishing both volume and the flow status through 1260 and 1265 before the rapid pressure increase. The two pulses immediately following the recharge pulse similarly determine a new volume and flow rate. This new rate, however, is subject to a significant flow acceleration component, which is made evident by the third sample after the pulse. The final settling into an exponential decay is indicated by the fourth sample after the pulse. The six samples, each time-smeared over known intervals, imply incoming and outgoing flows in a dynamic flow model. Interpretation of the data will be described at two levels: the simulation level, and the simplified controller algorithm level. The simulation interpretation is developed first in the R&D sequence, typically using high level software to interpret sampled data and simply learn how to arrive at the desired solution for volume delivered, regardless of computation time. The simplified algorithm, whose form can vary considerably, represents a synthesis, derived from the simulation interpretation, of a simple empirical formula that expresses, to good approximation, the results derived from the simulation.

For the simulation interpretation, one begins with the general dynamic description expressed by FIG. 12 and the equations shown above for reducing that figure to dynamic solutions. One codes software to express, in terms of the dynamic solution, what values one expects for the time-averaged volume samples over the pulse-high intervals of trace 1330. The inputs to the simulation are therefore the parameters of the system, including source and sink pressures, fluid density and viscosity, variables related to the geometry of the fluid controller system, and variables describing such things as tube set wave impedance and load impedance. The outputs are simulated volume samples. In an actual device, one has a number of the components of FIG. 12 reproduced fairly repeatably in successive flow control hardware units. The parameters corresponding to these controlled variables are taken as fixed constants, reducing the number of undetermined inputs to the simulation. Some of the system components will vary in the field, e.g., if different tube sets might be connected to the controller output, or if it proves that certain dynamic characteristics of the controller are not readily standardized and are likely to vary significantly from unit to unit. The uncontrolled parameters remain as unknown parameters of the model, while controlled parameters, e.g., the properties of the DVC volume sensing device, are removed from the list of unknowns. Source and sink pressures are among the unknown parameters. The problem at hand is then a variation on the well-explored but nonetheless challenging computational problem of functional minimization. As components of an input vector, one has the values of the unknown variables. As an output vector, one has a number (six in this example) of simulated volume averages, computed over the pulse-high sampling intervals of trace 1330. Then one has an equal number of empirically-measured volume averages. The output vector from the simulation, minus the empirically-measured vector, defines an error vector. The functional minimization problem is to vary the unknown parameters of the model to minimize the error vector. In general, one needs at least as many components of error vector as one has unknown system parameters to be determined, otherwise the error vector will not define the input vector uniquely.

Once the simulation model is running and successfully incorporated into a functional minimization routine, then one obtains system parameters computed from volume measurements. One inferred system parameter is of particular importance: the total fluid volume that passes through valve 1225 during the interval when 1320 is high. Given that, one knows how much volume is ultimately delivered to the fluid sink. The challenge is to estimate how much the minimum-to-maximum peak swing of trace 1310 is reduced by fluid flowing out through components 1260 and 1265 during the valve-open interval. Correcting for this reduction will yield the desired volume through 1225. Two other parameters are of operational importance: source and sink pressures. The functional minimization program yields each of these three parameters (i.e. input volume bolus, source pressure, and sink pressure) as three numerical functions of the values of the time-averaged volume samples. In the simulation and functional minimization process, it was necessary to solve for all the other unknowns of the system as well, but the remainder of the solution need not be embodied in the controller algorithm.

From the information obtained, the reduction of the simulation-derived relationships to a simplified algorithm for use, e.g., in an embedded controller algorithm, is developed. As a concrete example of such a simplified algorithm, suppose one takes the two volume, samples just preceding the valve pulse and extrapolates from them a straight line forward to a "volume" at the midpoint of the valve pulse. Suppose one similarly takes the two volume samples immediately following the valve pulse and extrapolates from them a straight line back to a "volume" at the midpoint of the valve pulse. The difference between these forward and backward-extrapolated volumes is nearly equal to the volume that flowed in through valve 1225. These volumes, summed over pulses, are the volumes that ultimately reach the fluid load, e.g., the patient. If one wants a more accurate algorithm, one can incorporate moire sample values and infer second-derivative corrections for the extrapolations just described, or one can make greater use of known properties of the dynamic model. Whatever level of sophistication is attained, the simulation model, empirically matched to a bench prototype of a real, instrumented fluid delivery system, is a computational standard against which controller algorithms can be evaluated.

An alternative to the simulation and functional minimization standard is purely experimental, the results of an instrumented bench setup in which delivered volumes are measured independently while the system is operated over varying conditions, yielding data sets of volume-sensor samples and actual delivered volumes. One can derive controller software that works well with such data sets.

Still another alternative for volume bolus determination is pure curve fitting, with only a minor adjustment of the method based on empirical measurements. Ignoring the dynamic details behind the curves, one has a region of volume decay approaching the upswing region, a discontinuity in derivatives followed by a rapid volume upswing, a second discontinuity in derivatives, and a curve emerging from the upswing region. The curves on either side of the upswing region can be extrapolated without any reference to the underlying dynamics, provided that the first derivative is continuous and does not change too rapidly on a time scale comparable in duration to the valve pulse width. A delta volume should then be computed between the forward- and backward-extrapolated curves, selecting some time point within the valve pulse interval for computing that difference. The simplified description above suggested linear extrapolations and the mid-point of the pulse interval. A better result would be obtained, e.g., by quadratic extrapolations (possibly calling for a different distribution of volume samples than is illustrated in trace 1330), and choosing a time point within the pulse interval that is a midpoint not in time, but for change in flow rate out toward the fluid load. This midpoint in rate change will lie, on a time scale, close to the midpoint of a half-cycle pulse interval, and past the midpoint of short pulse intervals in the fluid acceleration domain. Two values for the selected fraction of the valve pulse interval at which volume extrapolations are subtracted, one time-fraction for fixed-maximum-bolus mode and another time-fraction for small-variable-bolus mode, used in conjunction with extrapolation algorithms, would describe a relatively simple volume estimation algorithm relying minimally on a system dynamic description.

There are many possible algorithms, of which the good ones have in common that they yield the same, correct, results. In many contexts, the linear-extrapolation model described above for volume delivery inference is fully adequate. For determining pressure at the fluid sink, a simple solution lies in looking at the decay of flow rate with decline in sensor pressure (where this sensor pressure is itself a calibrated function of the primary volume reading.) The sensor pressure at which flow rate extrapolates to zero in an exponential decay is the load pressure. The source pressure is inferred from the bolus size that enters the sensor when the valve opens for any given, fixed interval. That bolus size at fixed pulse width varies linearly as a function of sensor pressure at the moment of valve opening. When the sensor pressure is equal to the source pressure the bolus size extrapolates to zero. To help determine source pressure, the volume sensor pressure can be varied intentionally by momentarily speeding up and then slowing down infusion, on a time scale short enough to be of no significance to the long-term delivery. These rate variations, reflected as pressure variations into the load, will reveal the change in source bolus volumes with sensor pressure, yielding the desired extrapolation to source pressure. Any further algorithmic sophistication in deriving source pressure lies in inferring, as accurately as possible, just what the bolus size is that flows into the volume displacement sensor as fluid simultaneously flows out toward the fluid sink.

Moving to FIG. 14, we find a volume trace 1410 analogous to trace 1310, starting with about the same fluid acceleration When the valve opens, except that the volume increase in truncated by a much earlier valve closure. A little ringing is shown at the valve closure, due to small compliances, e.g., in valve disk 210. The dynamic processes of rapid flow acceleration followed by gradual flow deceleration toward the fluid load are like those discussed earlier in relation to FIG. 13. A similar algorithmic determination of volume delivered with each pulse is performed. Flow target logic such as was described for the preferred embodiment keeps net infused volume very close to the moving infusion target.

The reader will appreciate the potential variability in the design process based on the fairly detailed guidelines provided above. A procedure has been described to design and fabricate a fluid delivery system and develop software algorithms, linked to a dynamic understanding of the hardware, to achieve accurate volumetric fluid delivery in an economical package with low energy requirements. The breadth of the invention, going beyond the particulars used for concrete examples of embodiments above, will be seen in the following claims.

I claim:

1. A system for controlling the flow of a fluid from a source to a sink comprising:
   a. a source valve couplable to a fluid source containing a deliverable fluid, wherein said source valve is capable of regulating flow of said deliverable fluid from said source;
   b. a fluid pathway connecting said source valve to a sink;
   c. a volume displacement sensor couplable to said fluid pathway, wherein said sensor converts displacement into an electrical signal; and
   d. controller means responsive to said electrical signal from said sensor, said controller means acting on said source valve so that said source valve delivers a controlled selectable bolus volume of said deliverable fluid to said sink.

2. The system as claimed in claim 1 wherein said source valve is positioned between said fluid source and said volume displacement sensor, said system further comprising a second valve coupled between said volume displacement sensor and said sink with said controller means acting on said second valve so as to aid in the delivery of said controlled selectable volume of said deliverable fluid to said sink.

3. The system as claimed in claim 1 wherein said controller means includes means for delivering said fluid to said sink at a controllable variable bolus frequency so as to provide a variable prescribed average volumetric flow rate of said fluid.

4. The system as claimed in claim 3 wherein said sink is a patient.

5. A system for controlling the flow of a deliverable fluid from a source to a sink, wherein source pressure exceeds sink pressure, comprising:
   a. a disposable cassette coupled to said source, said disposable cassette comprising source opening/closing means in contact with a source valve, wherein said source valve is coupled to a deliverable fluid source of said source via a fluid pathway; and b. a reusable controller section comprising:
   i. a volume displacement sensor coupled to said fluid pathway, wherein said sensor converts displacement into an electrical signal; and
   ii. controller means responsive to said electrical signal from said sensor, said controller means acting on said source valve so that said source valve delivers a controlled selectable bolus volume of said deliverable fluid to said sink.

6. The system as claimed in claim 5 further comprising a sink valve coupled between said volume displacement sensor and said sink with said controller means acting on said sink valve so that said sink valve aids in the delivery of said controlled selectable volume of said deliverable fluid to said sink, and wherein said disposable cassette includes sink opening/closing means in contact with said sink valve.

7. The system as claimed in claim 6 wherein said source opening/closing means includes a source valve actuator component and said sink opening/closing means includes a sink actuator component, wherein said actuator components open and close said source valve and said sink valve quickly.

8. The system as claimed in claim 5 with said volume displacement sensor comprising a sensor cavity having an incompressible volume transfer fluid contained therein, wherein said incompressible volume transfer fluid is volumetrically displaced by said deliverable fluid when said deliverable fluid moves from said source to said sink.

9. The system as claimed in claim 8 wherein said sensor cavity includes barrier means between said incompressible volume transfer fluid and said deliverable fluid.

10. The system as claimed in claim 9 wherein said barrier means comprises a reusable fluid-impermeable elastic material.

11. The system as claimed in claim 9 with said volume displacement sensor further comprising a volume displacement interface between said barrier means and said deliverable fluid, wherein said volume displacement interface prevents mixing of said incompressible volume transfer fluid and said deliverable fluid.

12. The system as claimed in claim 7 wherein said source actuator and said sink actuator are electrical solenoids.

13. The system as claimed in claim 7 wherein said source actuator and said sink actuator are voice-coil drivers.

14. The system as claimed in claim 7 wherein said source actuator and said sink actuator are piezoelectric transducers.

15. The system as claimed in claim 7 with said controller section further comprising means for determining said timing of the opening and closing of said source and sink valves, said determination means comprising:

a. means for converting said electrical signal into a linear measure of volume;
   b. computation means responsive to said linear measure of volume and controlling said timing to achieve a prescribed average volumetric flow rate;
   c. as part of said computation means, means for computing from said linear measure a measure of volume transfer from said source to said sink; and
   d. as part of said computation means, means for adjusting timing of said source and sink valves, responsive to said measure of volume transfer, and responsive to said prescribed average volumetric flow rate, causing said measure of volume transfer to cumulatively approximate said prescribed average volumetric flow rate.

16. The system as claimed in claim 15 further including, as part of said means for adjusting said timing of said source and sink valves, means for setting valve-open timing periods to yield deliverable fluid flow for approximately half the natural period of oscillation of volume to and from said volume displacement sensor via the open one of said source and sink valves.

17. The system as claimed in claim 15 further including, as part of said means for adjusting said timing of said source and sink valves, means for setting valve-open timing periods to yield deliverable fluid flow for substantially less than half the natural period of oscillation of volume of deliverable fluid to and from said volume displacement sensor via the open one of said source and sink valves.

18. The system as claimed in claim 15 further including means for converting said electrical signal into a linear measure of pressure, and, as part of said computation means, means to determine pressures at said fluid source and said fluid sink.

19. A dynamic system for variably controlling average volumetric flow rate driven by a variable fluid pressure differential from a source to a sink by use of variable valve timing, volume displacement sensing, and flow restriction, including:

a. a fluid source and a fluid sink wherein source pressure exceeds sink pressure;
   b. a source valve capable of opening and closing quickly under electronic control, wherein said source valve regulates the flow of deliverable fluid from said source;
   c. a volume displacement sensor for receiving said deliverable fluid from said source via said source valve, wherein said volume displacement sensor includes means to convert volume displacement into a quantifiable electrical signal;
   d. a flow restrictor between said sensor and said sink, said flow restrictor for regulating flow rate of said deliverable fluid from said sensor in relation to pressure in said sensor and in said sink; and
   e. controller means responsive to said electrical signal, wherein said controller means controls the timing of said opening and closing quickly of said source valve to achieve controllable variable fluid bolus size and frequency into said sensor so as to provide a variable prescribed average volumetric flow rate of said deliverable fluid from said sensor via said flow restriction into said sink.

20. A system for controlling the flow of a fluid from a source to a sink comprising:

a. a fluid pathway for coupling said source to said sink;
   b. a valve couplable to said fluid pathway, wherein said valve is capable of regulating flow of said deliverable fluid within said fluid pathway;
   c. a volume displacement sensor couplable to said fluid pathway, wherein said sensor is capable of converting displacement of said fluid into an electrical signal; and
   d. controller means responsive to said electrical signal from said sensor, said controller means capable of acting on said valve so that said valve delivers a controlled selectable bolus volume of said deliverable fluid to said sink.

* * * * *